United States Patent
Dolle, III et al.

Patent Number: 5,948,696
Date of Patent: Sep. 7, 1999

[54] COMBINATORIAL BIARYL AMINO ACID AMIDE LIBRARIES

[75] Inventors: Roland Ellwood Dolle, III, King of Prussia, Pa.; Brian Francis McGuinness, Plainsboro; Zahid Hussain, Highland Park, both of N.J.

[73] Assignee: Pharmacopeia, Inc., Princeton, N.J.

[21] Appl. No.: 08/876,853

[22] Filed: Jun. 16, 1997

[51] Int. Cl.[6] ............... G01N 33/543; G01N 33/551; G01N 33/544; A61K 38/00
[52] U.S. Cl. ............... 436/518; 436/524; 436/527; 436/530; 436/501; 530/333; 530/334
[58] Field of Search .................. 436/518, 501, 436/524, 527, 530, 56; 530/333, 334

[56] References Cited

U.S. PATENT DOCUMENTS

| | | | |
|---|---|---|---|
| 5,481,020 | 1/1996 | Ng et al. | 560/27 |
| 5,734,054 | 3/1998 | Dolle, III et al. | 544/390 |
| 5,766,963 | 6/1998 | Baldwin et al. | 436/518 |

FOREIGN PATENT DOCUMENTS

WO95/04072  2/1995  WIPO.

OTHER PUBLICATIONS

Zuckermann et al. "Discovery of Nanomolar Ligands for 7–Transmembrane G–Protein–Coupled . . . " *J. Med. Chem.* 37, 2678–2685 (1994).

Shieh et al. "A Simple Asymmetric Synthesis of 4–Arylphenylalanines via Palladium–Catalyzed . . . " *J. Org. Chem.* 57, 379–381 (1992).

Burk et al. "Versatile Tandem Catalysis Procedure for the Preparation of Novel . . . " *J. Am. Chem. Soc.* 116, 10847–10848 (1994).

Ksander et al. "Dicarboxylic Acid Dipeptide Neutral Endopeptidase Inhibitors" *J. Med. Chem.* 38, 1689–1700 (1995).

Guiles et al. "Solid–Phase Suzuki Coupling for C–C Bond Formation" *J. Org. Chem.* 61, 5169–5171 (1996).

Frenette et al. "Biaryl Synthesis via Suzuki Coupling on a Solid Support" *Tetrahedron Letters* 35, 9177–9180 (1994).

Han et al. "Silicon Directed ipso–Substitution of Polymer Bound Arylsilanes: . . . " *Tetrahedron Letters* 37, 2703–2706 (1996).

Martin et al. "Palladium–Catalyzed Cross–Coupling Reactions of Organoboronic . . . " *Acta Chemica Scandinavica* 47, 221–230 (1993).

*Primary Examiner*—Ponnathapura Achutamurthy
*Assistant Examiner*—P. Ponnaluri
*Attorney, Agent, or Firm*—Heslin & Rothenberg, P.C.

[57] ABSTRACT

Combinatorial chemical libraries of the Formula [S]-C(O)-L'-Z containing biaryl amino acids are disclosed, in which [S] represents a solid support and -L'-Z is a linker/compound residue. In these libraries, Z is —$NR^1R^2$. $R^1$ is chosen from H, $C_1$ to $C_{20}$ hydrocarbon, heteroaralkyl, heterocycloalkyl, substituted arylalkyl, alkoxyalkyl or alkyl-$SO_2$NH-alkyl and $R^4$ is an acyl or sulfonyl residue. $R^2$ is chosen from

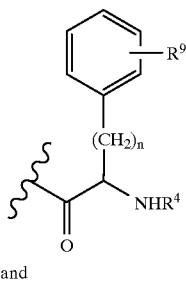

and

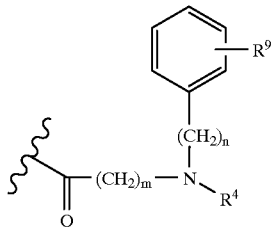

The combinatorial libraries are optionally encoded with tags. The use of these libraries in assays to discover biologically active compounds is also disclosed.

10 Claims, No Drawings

COMBINATORIAL BIARYL AMINO ACID AMIDE LIBRARIES

TECHNICAL FIELD

This invention relates generally to the synthesis of chemical compounds, and more particularly, to the synthesis of combinatorial libraries of biaryl-containing amino acid amides.

BACKGROUND OF THE INVENTION

Methods for the synthesis of large numbers of diverse compounds which can be screened for various possible physiological or other activities are of interest (Ellman, et. at. *Chem. Rev.* 96: 555–600 (1996)). Techniques have been developed in which individual units are added sequentially as part of the chemical synthesis to produce all or a substantial number of the possible compounds which can result from all the different choices possible at each sequential stage of the synthesis. For these techniques to be successful, it is necessary for the compounds to be amenable to methods by which one can determine the structure of the compounds so made. Examples of such techniques include, the technique of Brenner and Lerner (*PNAS USA* 81: 5381–83 (1992)) and WO 93/20242, according to which oligonucleotides are produced in parallel, with and are chemically linked as genetic tags, to oligopeptides as the compounds of interest. WO 93/06121 teaches methods for particles-based synthesis of random oligomers wherein identification tags on the particles are used to facilitate identification of the oligomer sequence synthesized. Ohlmeyer et al., (*Proc. Natl. Acad. Sci.* USA, 90, 10922–10926, 1993) discloses a detachable tagging system.

SUMMARY OF THE INVENTION

The present invention relates to combinatorial libraries of compounds optionally encoded with tags, and to the use of these libraries in assays to discover biologically active compounds. The present invention also relates to a library of compounds comprising amino acid amides containing a biaryl group and to the use of the libraries to identify biologically active members by screening bioassays.

In one aspect, the invention relates to a combinatorial chemical library comprising a plurality of members of the Formula I:

$$(T\text{-}L)q\text{-}[S]\text{-}C(O)\text{-}L'\text{-}Z \qquad \text{I}$$

or I'

$$[S]\text{-}C(O)\text{-}L'\text{-}Z \qquad \text{I'}$$

wherein:

[S] is a solid support;
T-L is an identifier residue;
L'-Z is a linker/compound residue; and
q is 2–30;
Z is —$NR^1R^2$;
$R^1$ is chosen from H, $C_1$ to $C_{20}$ hydrocarbon, heteroaralkyl, heterocycloalkyl, substituted arylalkyl, alkoxyalkyl or alkyl-$SO_2NH$-alkyl;

$R^2$ is chosen from

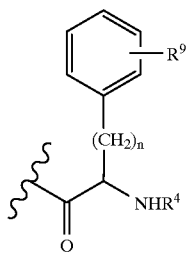

and

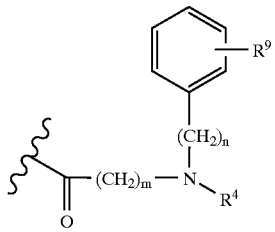

$R^4$ is chosen from —$COR^5$, —$COOR^5$, —CO—$(CH_2)_pR^6$, —$SO_2R^7$, —$CONHSO_2R^7$, and —$CONHR^7$;

$R^5$ is chosen from alkyl, substituted alkyl, cycloalkyl, heterocycloalkvl, aryl, aralky, heteroaryl, and heteroaralkyl;

$R^6$ is chosen from alkoxy, alkoxy-$CH_2(CH_2)_pO$—, aryl, heteroaryl, dialkylamino, —$CH_2CO_2R^8$, and —$OCH_2CO_2R^8$;

$R^7$ is chosen from alkyl, aryl, and aralkyl;

$R^8$ is chosen from H and alkyl;

$R^9$ is chosen from H, halo, alkyl, aralkyl, aryl, heteroaryl, and

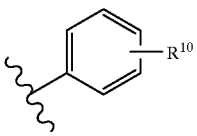

$R^{10}$ is chosen from —CHO, —$CH_2NHR^{11}$, —NH-acyl, —$CH_2N(acyl)R^{11}$, $CH_2OH$, aryl, cycloalkyl, aralkyl, carboxyl, 1-(trityl)tetrazol-2-yl, tetrazol-2-yl, —CH(OH)C(CH$_3$)$_2$CO$_2$R$^8$, —CH(OH)CH$_2$CH=CH$_2$, —CH[NH(CH$_2$)$_s$R$^{12}$]C(CH$_3$)$_2$CO$_2$R$^8$, —CH=CHR$^{16}$ and

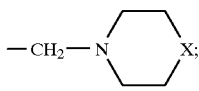

$R^{11}$ is chosen from alkyl, —$CH_2(CH_2)_s$-alkoxy, —$(CH_2)_sCH_2OH$, aralkyl, -alkyl-$NHSO_2$-alkyl, heteroaralkyl, —$(CH_2)_sCH_2NR^{12}R^{12}$, —$CH(R^{15})CONR^{13}R^{14}$, and

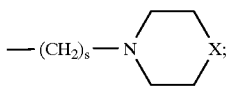

$R^{12}$ is independently selected from alkyl, aryl and aralkyl;

$R^{13}$ and $R^{14}$ are independently selected from H, alkyl, and aralkyl;

$R^{15}$ is chosen from H, alkyl, cycloalkyl, aralkyl, aryl, and heteroaryl;

$R^{16}$ is chosen from $C_1$ to $C_{20}$ hydrocarbon, heteroaryl and $COOR^8$;

X is chosen from $CH_2$, O, S, or $NR^{15}$; and m, n, p and s are independently 1–4.

In a preferred embodiment, $R^5$ is one or more of lower alkyl and substituted alkyl; $R^7$ is one or more of lower alkyl and aryl; $R^8$ is one or more of H and lower alkyl; $R^9$ is one or more of halo, alkyl, aralkyl, aryl, heteroaryl, and

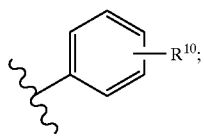

$R^{10}$ is one or more of $CH_2NHR^{11}$, —NH-acyl, —$CH_2OH$, carboxyl, 1-(trityl)tetrazol-2-yl, tetrazol-2-yl, —CH(OH)C$(CH_3)_2CO_2R^8$, —CH[NH$(CH_2)_sR^{12}$]C$(CH_3)_2CO_2R^8$ and

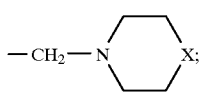

$R^{12}$ is one or more of lower alkyl and aryl; $R^{13}$ and $R^{14}$ are H; $R^{15}$ is one or more of H and heteroaryl; X is one or more of O and $NR^{15}$; m and p are 1; and n and s are 1 or 2.

In another preferred embodiment, $R^1$ is chosen from methyl; cyclopropylmethyl; butyl; methoxyethyl; tetrahydrofuran-2-ylmethyl; cis-myrtanyl; 4-phenylbutyl; 2-chlorobenzyl; 3,4-dichlorobenzyl; 4-methoxybenzyl; 3,4-dimethoxyphenethyl, 3-picolyl, N-morpholinylethyl; methylsulfonamidopropyl; and 1-imidazolylpropyl.

In another preferred embodiment, $R^4$ is chosen from

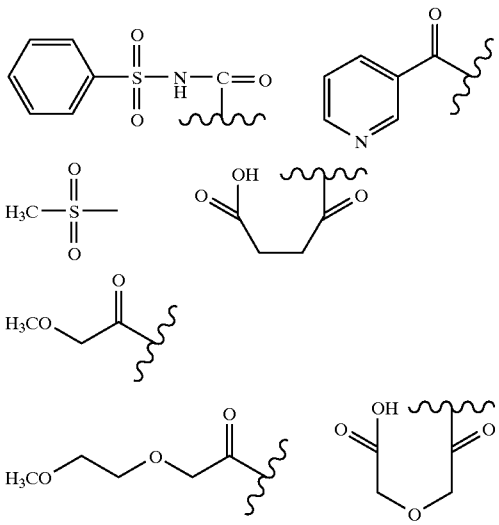

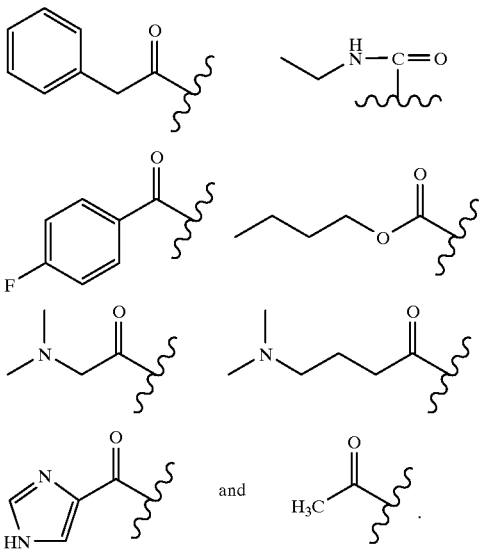

In another preferred embodiment, $R^9$ is chosen from 4-methoxyphenyl; phenyl; 2-methoxyphenyl; pyridin-3-yl; 3,5-bis(trifluoromethyl)phenyl; thien-2-yl; thien-3-yl; 3-methylthien-2-yl; benzofuran-2-yl: indol-5-yl; 3-methoxyphenyl; 3,4-methylenedioxyphenyl; furan-3-yl; 2,4,6-trimethylphenyl; 2,4-dichlorophenyl; 4-carboxyphenyl; 3-carboxyphenyl; 3,5-dichlorophenyl; 3,4-dichlorophenyl; furan-2-yl; 3-acetamidophenyl; 2-(tetrazol-2-yl)phenyl; benzyl; butyl; and 4-hydroxyphenyl. Alternatively, $R^9$ may be

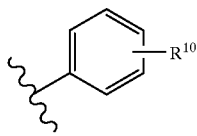

wherein $R^{10}$ is $CH_2NHR^{11}$ and $R^{11}$ is chosen from methoxyethyl, isopropyl, 2-hydroxyethyl, benzyl, 3-picolinyl, 3-(1-imidazolyl)propyl; N-morpholinylethyl; methylsulfonamidopropyl; and 3-(dimethylamino)propyl; or $R^{10}$ may be chosen from

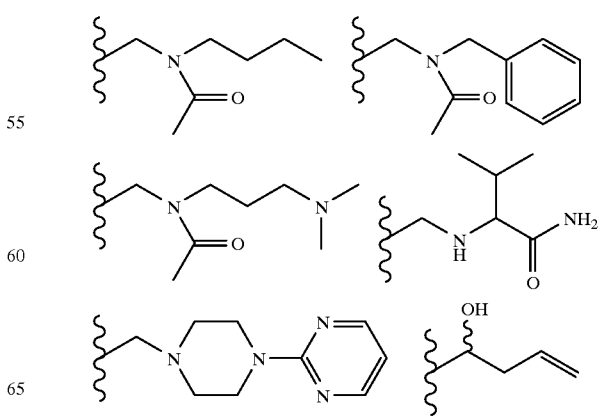

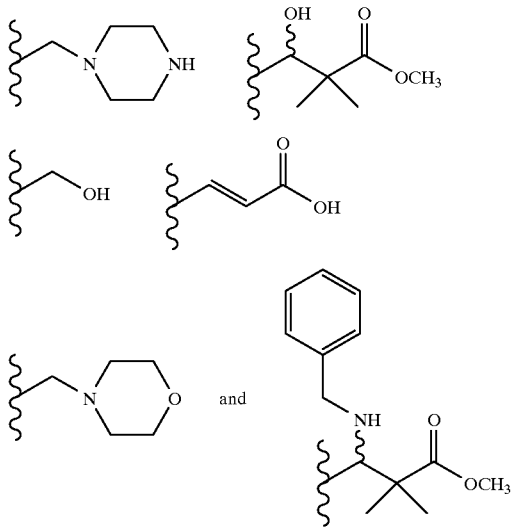

In another preferred embodiment, the identifier residue, T'-L, is of the Formula II or IIa

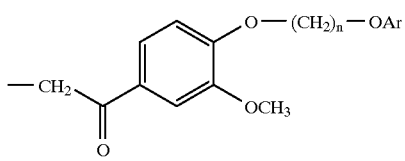

or

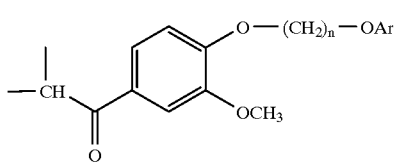

wherein: n and q are 3–12 and Ar is halophenyl. More preferred libraries of Formula I are those wherein n is 4–12 and Ar is pentachlorophenyl, or n is 3–6 and Ar is 2,4,6-trichlorophenyl.

Other preferred libraries of Formula I are those wherein -L'- is

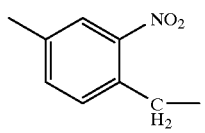

such that the left-hand bond as shown is the point of attachment to —C(O)— the and the right hand bond is the point of attachment to -Z.

Depending on the choice of L' (see Table 1), the compounds or ligands -Z of Formula I may be detached by photolytic, oxidative, acidic, basic, or other cleavage techniques. For example, when -L'- is given by (a), photolytic cleavage may be represented by:

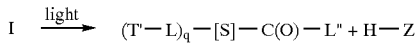

wherein L" is the residue from L' and H-Z is given by Formula III:

$$NHR^1R^2 \qquad III$$

One aspect of the invention is the use of the combinatorial library of Formula I in assays to discovery biologically active compounds or ligands of Formula III. Thus an another aspect of the invention is a method of identifying a compound having a desired characteristic which comprises synthesizing a combinatorial library of Formula I and testing the library of Formula I, either attached or detached from, the solid supports, in an assay which identifies compounds of Formula III having the desired characteristic. A further aspect of the invention is determining the structure of any compound so identified.

It is within the scope of the present invention that chemical structures of compounds identified as having a desired characteristic can be determined by either decoding the tags (T, T'-L- of Formula I) or by deconvolution of the library (Smith et al., *BioMed. Chem. Lett.*, 4, 2821 (1994); Kurth et al., *J. Org. Chem.*, 59, 5862 (1994); Murphy et al., *J. Am. Chem. Soc.*, 117, 7029 (1995); Campell et al., *J. Am. Chem. Soc.*, 118, 5381 (1995); and Erb et al., *Proc. Natl. Acad. Sci. USA*, 91, 11422 (1994)).

DETAILED DESCRIPTION OF THE INVENTION

Abbreviations and Definitions

The following abbreviations and terms have the indicated meanings throughout:

| | |
|---|---|
| Ac = | Acetyl |
| BNB = | 4-bromomethyl-3-nitrobenzoic acid |
| BOC = | t-butyloxy carbonyl |
| Bu = | butyl |
| c- = | cyclo |
| DBU = | Diazabicyclo[5.4.0]undec-7-ene |
| DCM = | Dichloromethane = methylene chloride = $CH_2Cl_2$ |
| DEAD = | Diethyl azodicarboxylate |
| DIC = | diisopropylcarbodiimide |
| DIEA = | diisopropylethyl amine |
| DMAP = | 4-N,N-dimethylaminopyridine |
| DMF = | N,N-dimethylformamide |
| DMSO = | Dimethyl sulfoxide |
| DVB = | 1,4-divinylbenzene |
| FACS = | fluorescence activated cell sorting |
| Fmoc = | 9-fluorenylmethoxycarbonyl |
| GC = | gas chromatography |
| HATU = | O-(7-Azabenzotriazol-1-yl)-1,1,3,3-tetramethyluronium hexafluorophosphate |
| HOAc = | acetic acid |
| HOBt = | hydroxybenzotriazole |
| m- = | meta |
| Me = | methyl |
| NMO = | N-methylmorpholine oxide |
| o- = | ortho |
| p- = | para |
| PEG = | polyethylene glycol |
| Ph = | phenyl |
| PhOH = | phenol |
| PfP = | pentafluorophenol |
| PyBroP = | bromo-tris-pyrrolidino-phosphonium hexafluorophosphate |
| rt = | room temperature |
| sat'd = | saturated |
| s- = | secondary |
| t- = | tertiary |

| | |
|---|---|
| TFA = | trifluoroacetic acid |
| THF = | tetrahydrofuran |
| TMOF = | trimethyl orthoformate |
| TMS = | trimethylsilyl |
| Trt = | triphenylmethyl |

"Alkyl" or "lower alkyl" is intended to include linear, or branched hydrocarbon structures and combinations thereof. "Lower alkyl" means alkyl groups of from 1 to 6 carbon atoms. Examples of lower alkyl groups include methyl, ethyl, propyl, isopropyl, butyl, s-and t-butyl, pentyl, hexyl, and the like.

"Cycloalkyl" or "lower cycloalkyl" includes cycloalkyl groups of from 3 to 12 carbon atoms. Examples of "cycloalkyl" or "lower cycloalkyl" groups include c-propyl, c-butyl, c-pentyl, c-hexyl, 2-methylcyclopropyl, cyclopropylmethyl, cyclopentylmethyl, norbornyl, adamantyl, myrtanyl and the like.

"Alkenyl" is $C_2$–$C_8$ alkenyl of a linear, branched, or cyclic ($C_5$–$C_6$) configuration and combinations thereof. Examples of alkenyl groups include vinyl, allyl, isopropenyl, pentenyl, hexenyl, c-hexenyl, 1-propenyl, 2-butenyl, 2-methyl-2-butenyl, and the like.

"Alkynyl" is $C_2$–$C_8$ alkynyl of a linear or branched configuration and combinations thereof. Examples of alkynyl groups include ethyne, propyne, butyne, pentyne, 3-methyl-1-butyne, 3,3-dimethyl-1-butyne, and the like.

$C_1$ to $C_{20}$ Hydrocarbon includes alkyl, cycloalkyl, alkenyl, alkynyl, aryl and combinations thereof. Examples include phenethyl, cyclohexylmethyl and naphthylethyl.

"Alkoxy" means alkoxy groups of from 1 to 8 carbon atoms of a straight, branched, cyclic configuration and combinations thereof. Examples of alkoxy groups include methoxy, ethoxy, propoxy, isopropoxy, cyclopropyloxy, cyclohexyloxy, and the like.

"Acylamino" means acylamino groups of from 1 to 8 carbon atoms of a straight, branched or cyclic configuration and combinations thereof. Examples of acylamino groups are acetylamino, butyrylamino, cyclohexylamino, and the like.

Halogen includes F, Cl, Br, and I, with F and Cl as the preferred groups.

"Halophenyl" means phenyl substituted by 1–5 halogen atoms. Halophenyl includes pentachlorophenyl, pentafluorophenyl, and 2,4,6-trichlorophenyl.

"Fluoroalkyl" refers to an alkyl residue in which one or more hydrogen atoms are replaced with F, for example: trifluoromethyl, difluoromethy, and pentafluoroethyl.

"Aryl" and "heteroaryl" mean a 5- or 6-membered aromatic or heteroaromatic ring containing 0–3 heteroatoms selected from O, N, and S; a bicyclic 9- or 10-membered aromatic or heteroaromatic ring system containing 0–3 heteroatoms selected from O, N, and S; or tricyclic 13- or 14-membered aromatic or heteroaromatic ring system containing 0–3 heteroatoms selected from O, N, and S; each of which rings is optionally substituted with chosen from lower alkyl, substituted alkyl, alkenyl, alkynyl, =O, $NO_2$, halogen, hydroxy, alkoxy, methylenedioxy, alkoxyethoxy, cyano, $NR^{18}R^{18}$, acylamino, perfluoroalkyl, phenyl, benzyl, trityl, phenoxy, naphthyloxy, aryloxy, benzyloxy, heteroaryl, and heteroaryl, and heteroaryloxy. Each of the foregoing phenyl, benzyl, phenoxy, benzyloxy, heteroaryl, and heteroaryloxy substituents may be optionally substituted with 1–3 substituents selected from lower alkyl, alkenyl, alkynyl, halogen, hydroxy, alkoxy, cyano, phenyl, benzyl, benzyloxy, caboxamido, heteroaryl, heteroaryloxy, $NO_2$, and $NR^{18}R^{18}$.

$R^{18}$ is independently H, alkyl, cycloalkyl, aryl, aralkyl, or —$R^{18}R^{18}$ may be fused to form a cyclic ring with nitrogen.

The aromatic 6- to 14-membered carbocyclic rings include benzene, naphthalene, indane, tetralin, and fluorene and the 5- to 10-membered aromatic heterocyclic rings include imidazole, pyridine, indole, thiophene, benzopyranone, thiazole, furan, benzimidazole, quinoline, isoquinoline, quinoxaline, pyrimidine, pryrazine, tetrazole, and pyrazole.

"Arylalkyl" denotes a residue comprising an alkyl attached to an aryl ring. Examples include benzyl, phenethyl, 4-chlorobenzyl, and the like.

"Heteroarylalkyl" denotes a residue comprising an alkyl attached to a heteroaryl ring such as pyridinylmethyl, pyrimidinylethyl, and the like.

"Heterocycloalkyl" means a cycloalkyl where one to two of the methylene ($CH_2$) groups is replaced with a heteroatom, such as O, NR (R=H, alkyl), S and the like. When two heteroatoms are separated by a single carbon, the resulting heterocycloalkyls tend to be unstable in aqueous solutions and are therefore not preferred. Examples of heterocycloalkyls include: tetrahydrofuranyl, piperidine, dioxanyl, and the like.

"Carboxyalkyl" and "acyl" refer to —C(O)R where R is alkyl.

"Substituted" alkyl, alkenyl, alkynyl, cycloalkyl, or heterocycloalkyl means alkyl, alkenyl, alkynyl, cycloalkyl, wherein hydrogen atoms are replaced by halogen, hydroxy, loweralkoxy, carboxy, carboalkoxy, carboxamido, cyano, carbonyl, $NO_2$, $NR^{18}R^{18}$; —$SR^{18}$, —$SOR^{18}$, —$SO_2R^{18}$, acylamino, amidino, guanidino, ureido, aryl, heteroaryl, phenyl, aralkyl, phenoxy, benzyloxy, naphthyloxy, aryloxy, heteroaryloxy, and substituted phenyl, benzyl, heteroaryl, phenoxy, benzyloxy, and heteroaryloxy.

For the purpose of the present invention, the term combinatorial library means a collection of molecules based on logical design and involving the selective combination of building blocks by means of simultaneous chemical reactions. Each species of molecule in the library is referred to as a member of the library.

The linkers may be any component capable of being selectively cleaved to release both T and Z from the solid support. See, e.g., Greene and Wuts, "Protective Groups in Organic Synthesis," 2nd ed., Wiley, 1991. Specific linkers L' are depicted in Table 1 (note that -L-=-C(O)L'- or —$CH_2$—C(O)L'-), which also shows cleavage reagents. In designing a synthetic scheme, L and L' are chosen such that they are orthogonally reactive, i.e., they allow for removal of either T or Z (where T=T'OH) without removal of the other since simultaneous cleavage of both T and Z from the solid support is disadvantageous. In the structures as shown, the left-hand bond is the point of attachment to the solid support (via —C(O)— for L' and —C(O)— or —$CH_2$C(O)— for L) and the right-hand bond is the point of attachment to either T or Z.

The tags of this invention, T, are chemical entities which possess several properties: they are detachable from the solid supports, preferably by photolysis or oxidation; they are individually differentiable, and preferably separable; they are stable under the synthetic conditions; they are capable of being detected at very low concentrations, e.g., $10^{-18}$ to $10^{-9}$ mole. Preferred tags are identifiable with readily available equipment which does not require sophisticated technical capabilities to operate, and they are relatively economical. The tags may be structurally related or unrelated, e.g., a homologous series, repetitive functional groups, related members of the Periodic Chart, different isotopes, combinations thereof, and the like. At the end of the combinatorial synthesis, to each solid support there will usually be attached at least 0.01 femtomol, usually 0.001–50 pmol, of each tag. The tags may be aliphatic, alicyclic, aromatic, heterocyclic, or combinations thereof. Distinguishing features may be the number of repetitive units, such as methylene groups in an alkyl moiety; alkyleneoxy groups in a polyalkyleneoxy moiety; halo groups in a polyhalo compound; α- and/or β-substituted ethylene groups where the substituents may be alkyl groups, alkoxy, carboxy, amino, halo, or the like; isotopes; etc. Suitable tags and methods for their employment are described in U.S. Pat. No. 5,565,324, the entire disclosure of which is incorporated herein by reference.

The materials upon which the combinatorial syntheses of the invention are performed are referred to as solid supports, beads, and resins. These terms are intended to include:

(a). beads, pellets, disks, fibers, gels, or particles such as cellulose beads, pore-glass beads, silica gels, polystyrene beads optionally cross-linked with divinylbenzene and optionally grafted with polyethylene glycol and optionally functionalized with amino, hydroxy, carboxy, or halo groups, grafted co-poly beads, poly-acrylamide beads, latex beads, dimethylacrylamide beads optionally cross-linked with N,N'-bis-acryloyl ethylene diamine, glass particles coated with hydrophobic polymer, etc., i.e., material having a rigid or semi-rigid surface; and (b). soluble supports such as polyethylene glycol or low molecular weight, non-cross-linked polystyrene.

Optical Isomers—Diastereomers—Geometric Isomers

Some of the compounds described herein contain one or more asymmetric centers and may thus give rise to enantiomers, diastereomers, and other stereoisometric forms which may be defined in terms of absolute stereochemistry as (R) or (S), or as (D) or (L) for amino acids. The present invention is meant to include all such possible diastereomers as well as their racemic and optically pure forms. Optically active (R) and (S), or (D and L), isomers may be prepared using chiral synthons or chiral reagents, or resolved using conventional techniques. When the compounds described herein contain olefinic double bonds or other centers of geometric asymmetry, and unless specified otherwise, it is intended to include both E and Z geometric isomers. Likewise, all tautomeric forms are intended to be included.

Utility

The library of the present invention is useful as a screening tool for discovering new lead structures by evaluation across an array of biological assays, including the discovery of selective inhibition patterns across isozymes. The library is thus a tool for drug discovery; i.e., as a means to discover novel lead compounds by screening the library against a variety of biological targets and to develop structure-activity relationships (SAR) in large families of related compounds. The library may be tested with the compounds attached to the solid supports as depicted in Formula I or I', or the compounds Z may be detached prior to evaluation. With the compounds of Formula I or I', screening assays such as FACS sorting and cell lawn assays may be used. A particularly useful lawn assay is described in U.S. patent application 08/553,056 (filed Nov. 3, 1995), the disclosure of which is incorporated herein by reference. When a compound is detached prior to evaluation, its relationship to its solid support is maintained, for example, by location within the grid of a standard 96-well plate or by location of activity on a lawn of cells. Whether the compounds are tested attached or detached from the solid supports, the tags attached to solid support associated with bioactivity may then be decoded to reveal the structural or synthetic history of the active compound (Ohlmeyer et al., *Proc. Natl. Acad. Sci., USA*, 90 10922–10926, December 1993 and Still et al., Complex Combinatorial Chemical Libraries Encoded with Tags, WO 94/08051) or, alternatively, the structures may be determined by deconvolution. The usefulness of such a library as a screening tool is demonstrated by Burbaum et al., *Proc. Natl. Acad. Sci., USA*, 92 6027–6031, June 1995, who describe the assaying of encoded combinatorial libraries for, e.g., carbonic anhydrase inhibition.

Assays for Determining Biological Activity

Assays for evaluating the compounds of the present invention are well known in the art. Although one usually does not know a priori in which specific assays a particular library compound or group of library compounds will have activity, useful screening systems for use in assaying libraries of the format described herein, in order to identify activity with respect to a wide variety of enzymes and molecule targets have been developed and are illustrated by the following example.

1. Xanthine Oxidase Inhibition

The following materials are used:

3.9 $\mu$M hypoxanthine 0.3 mM 4-aminoantipyrene 2 mM 3,5-dichloro-2-hydroxybenzenesulfonate 50 mM sodium phosphate buffer, pH 7.5

5 U/mL horseradish peroxidase (Sigma P-6782, 5500 U/5 mg)

3 nM xanthine oxidase (buttermilk, Sigma X-4500, 16 U/mL) inhibitor

Reactions are carried out in 24 $\mu$L total volume in 96-well U-bottom polypropylene microtiter dishes (Costar) containing the test compounds 8 $\mu$L of sodium phosphate buffer, pH 7.5, is added to each well. A substrate mixture is prepared on ice by mixing 0.53 mL sodium phosphate buffer, 0.4 mL 4-aminoantipyrene (0.61 mg/mL), 0.4 mL 3,5-dichloro-2-hydroxybenzenesulfonate (5.3 mg/mL), 4 $\mu$L horseradish peroxidase (Sigma P-6782, 5500 U/5 mg), and 128 $\mu$L hypoxanthine 920 $\mu$g/mL. 8 $\mu$L of the substrate mixture is then pipetted into each well. 8 $\mu$L xanthine oxidase (buttermilk, 9.0 nM, Sigma X-4500, 16 U/mL) in sodium phosphate buffer, pH 7.5 (or buffer alone as a control) is added last, directly into the reaction mixture. The plates are pulse-spun briefly in a tabletop centrifuge before reading absorbance. Absorbance is read using a dual kinetics program (490 minus 650 nm) for 15 min. at r.t. without automix, in a microplate reader (Molecular Devices Thermomax). Initial rates are calculated (Vmax program) and compared to those of reactions without inhibitor.

2. Plasmepsin II Inhibition

The assay mix contained 50 mM sodium acetate (pH 5.0), 1 mg/ml BSA, 0.01% Tween 20, 12.5% glycerol, 18% DMSO and 12 $\mu$M plasmepsin substrate. Twenty five $\mu$L of the assay mix was added to each well of a 96-well microtiter plate containing dried down bead eluate or empty control wells. The plates were then sonicated and mixed. 25 $\mu$L of 8 nM plasmepsin II, in 50 mM sodium acetate (pH 5.0), 1 mg/ml BSA, 0.01% Tween 20, and 12.5% glycerol, was added to the assay mix. The final concentrations were 4 nM plasmepsin II, 6 $\mu$M plasmepsin substrate, 9% DMSO, 50 mM sodium acetate (pH 5.0), 1 mg/ml BSA, 0.01% Tween 20, and 12.5% glycerol. The reaction was incubated for 10 minutes at 25° C. and then quenched by the addition of 25 $\mu$L of 1 M Tris (pH 8.5) and 50% DMSO to achieve a final concentration of 0.33 M Tris and 23% DMSO. The EDANS fluorescence was measured using a Tecan, SLT FluoStar fluorescence plate reader with an excitation filter of 350 nm and an emission filter 510 nm. The background was determined by 25 μL of 50 mM sodium acetate (pH 5.0), 1 mg/ml BSA, 0.01% Tween 20, and 12.5% glycerol without enzyme.

Other examples of assay methods for evaluating the compounds of the present invention are disclosed in the following references, which are incorporated herein by reference:

ACE Inhibition—Holmquist et al., "A Continuous Spectrophotometric Assay for Angiotensin Converting Enzyme", *Anal. Biochem.*, 95, 540–548 (1979).

Thrombin Inhibition—Lottenberg et al., "Assay of Coagulation Proteases Using Peptide Chromogenic and Fluorogenic Substrates", *Meth. in Enzymol.*, 80, 341–361, (1981).

Carbonic Anhydrase Inhibition—Maren and Couto, "The Nature of Anion Inhibition of Human Red Cell Carbonic Anhydrases", *Archiv. of Biochem. and Biophy.*, 196, No. 2, September, 501–510 (1979).

Carbonic Anhydrase Inhibition—Ponticelo et al., "Thienothiopyran-2-sulfonamides: A Novel Class of Water-Soluble Carbonic Anhydrase Inhibitors", *J. Med. Chem.*, 30, 591–597 (1987).

Methods of Synthesis

The compounds of the present invention can be prepared according to the following methods. During each step in the syntheses that follow, each solid support upon which a compound is being synthesized, is uniquely tagged to define the particular chemical event(s) occurring during that step. The tagging is accomplished using identifiers such as those of Formula II, which record the sequential events to which the support is exposed during the synthesis. Tagging thus provides a reaction history for the compound produced on each support. The identifiers are used in combination with one another to form a binary or higher order encoding scheme permitting a relatively small number of identifiers to encode a relatively large number of reaction products. For example, when used in a binary code, N identifiers can encode up to $2^N$ different compounds and/or conditions. By associating each variable or combination of variables at each step of the synthesis with a combination of identifiers which uniquely define the chosen variables such as reactant, reagent, reaction conditions, or combinations of these, one can use identifiers to define the reaction history of each solid support.

In carrying out the syntheses, one begins with at least $10^4$, desirably at least $10^7$, and generally not exceeding $10^{15}$ solid supports. Depending on the pre-determined number of $R^1$ choices for the first step, one divides the supports accordingly into as many containers. The appropriate reagents and reaction conditions are applied to each container and the combination of identifiers which encode for each $R^1$ choice is added and attached. Depending on the chemistries involved, the tagging may be done prior to, concomitantly with, or after the reactions which comprise each choice. As a control, sample supports may be picked at any stage and a portion of their tags are analyzed. As needed, one may wash the beads free of any excess reagents or by-products before proceeding. At the end of each step, the supports are combined, mixed, and again divided, this time into as many containers as pre-determined for the number of $R^2$ choices for the second step in the synthesis. This procedure of dividing, reacting, tagging, and remixing is repeated until the combinatorial synthesis is completed.

A. Scheme 1: Derivatizing Rresin with Bis-Boc Lysine.

A batch of amino-functionalized PEG-grafted polystyrene beads, e.g. TentaGel™ amine 1, is equally divided into a pre-determined number of reaction vessels corresponding to the number of amines to be added to the resin in Step 2. In this instance, since 15 amines are used in the first combinatorial step, in 15 reaction vessels are placed equal portions of resin. The TentaGel resin may be modified with bis-Fmoc lysine 2 to increase the available reaction sites for ligand attachment. Bis-Fmoc lysine 2 is coupled to amino-functionalized TentaGel 1 by amide bond formation. Coupling is achieved by reacting a suspension of 1 in DMF with 2, HOBt and DIC. The suspension is shaken overnight, then drained or filtered and washed in succession with DMF, DCM, and DMF.

Identifiers are now added prior to addition of the photolabile linker and residues $R^1$. Unique tagging of the supports in each reaction vessel is achieved with combinations of identifiers encoded in a binary scheme, e.g., as depicted in Table 2, for the fifteen choices of $R^1$. The identifiers are attached by adding a solution of up to two identifiers in DCM (in a 7.5–15% wt./wt. identifier: solid support ratio, depending on the signal strength of the identifier) to a batch of supports suspended in ethyl acetate or DCM and shaking the mixture for 0.5–1 hr. A dilute solution of rhodium trifluoroacetate dimer is added and the mixture is shaken for an additional 1 h whereupon a second equal portion of identifier is added. This mixture is shaken overnight. The resin is then washed in DCM, methanol, and DCM. The procedure is repeated as necessary to add additional identifiers. For the purposes of simplicity, the identifiers are not shown in the schematics.

Scheme 2a

The Fmoc-protecting group on resin 3 is removed and 4-bromomethyl-3-nitrobenzoic acid (BNB) is attached. This is accomplished by the following method. A suspension of tagged resin 3 in piperidine/DMF is shaken about 1 hr, then washed with DMF and DCM. This bis-amine resin 4 is suspended in DMF, and treated with a solution of BNB, HOBt, DIC in DCM/MF. The suspension is shaken overnight, then drained and the resin is washed with DMF and DCM. This is repeated for each of the fifteen reaction vessels.

Scheme 2b

The fifteen batches of tagged BNB resin 6 are reacted with a unique primary amine (e.g., see Table 2) to generate resin 7. The coupling of each amine occurs through displacement of the linker bromide and formation of a new carbon-nitrogen bond. The amine is added to a suspension of resin 6 in THF and the mixture is shaken overnight. The mixture is drained and the resin is washed with DMF, DIEA/DMF, DMF, and DCM. This procedure is repeated for each of the fifteen reaction vessels.

The amine resins 7 are pooled, mixed, and divided into a pre-determined number of reaction vessels. In this instance, since seven iodoaryl pieces are used in the second combinatorial step, and since two vessels are used for each piece to accommodate the large volume of resin, the resin is divided in equal portions into fourteen vessels.

Scheme 3a

The mixtures of amine resins 7 are coupled with a Boc-iodophenylalanine corresponding to one of the three $R^2$ choices in Table 3, by amide bond formation. This is accomplished by the following method. Each amine resin 7 is suspended in a mixture of a Boc-iodophenylalanine, PyBroP®, and DIEA in DCM/DMF. The mixture is shaken overnight, drained, and the resin is washed with DMF and DCM. This procedure is repeated for the addition of the three Boc-iodophenylalanine pieces.

Scheme 4

The remaining four mixtures of amine 7 are all coupled with bromoacetic acid by reacting in DCM with DIC overnight. It will be apparent to the person of skill that bromoacetic acid could be replaced by any ω-bromoacid to generate the corresponding residue wherein m is other than 1. The resin is washed with DMF, DCM, DMF, and DMSO. The 4 batches of bromoacetate-modified resin 11 are reacted with a unique iodoarylamine (e.g., see Table 4). This is accomplished by the following method. The bromoacetate-modified resin 11 is treated with iodoaryl amine and DIEA in DMSO. The coupling of the amine to resin 11 occurs through bromide displacement. The resin is washed with DMSO, DMF, and DCM. The generated secondary amine 13 is protonated prior to tagging by shaking in TFA/DCM for about 15 minutes and then washing with DCM.

Unique tagging of the supports in each reaction vessel is achieved with combinations of identifiers encoded in a binary scheme, e.g., as depicted in Tables 3 and 4 for 7 choices of $R^2$. The identifiers are attached by adding a solution of up to two identifiers in DCM (in a 7.5–15% wt./wt. identifier: solid support ratio, depending on the signal strength of the identifier) to a batch of supports suspended in ethyl acetate or DCM and shaking the mixture for 0.5–1 hr. A dilute solution of rhodium trifluoroacetate dimer is added and the mixture is shaken for an additional 1 h whereupon a second equal portion of identifier is added and the mixture is shaken overnight. The resin is then washed in DCM, methanol, and DCM. The procedure is repeated as necessary to add additional identifiers.

Scheme 3b

The Boc protecting group is removed from resin 9 by treatment with TFA/DCM for about 30 minutes. The resin is drained and washed with DCM, methanol, and DCM to generate resin 10.

Scheme 5

The resin-bound aryliodides 10 and 13 are pooled, deprotonated with DIEA/DMF, washed with DCM and methanol, generating resin 14, which is mixed, and divided into a pre-determined number of reaction vessels. In this instance, since fifteen amino-capping groups are used in the third combinatorial step, the resin is divided in equal portions into fifteen vessels. Each vessel is reacted with a unique amine-capping reagent (see Table 5). The carboxylic acid reagents are coupled to resin 14 by amide bond formation either using HATU or PyBroP and DIEA in DMF or DIC in DCM. The anhydride reagents are reacted in DCM or DCM/DMF either with or without DIEA. The acid and sulfonyl chloride reagents are reacted in DIEA/DCM. The isocyanate reagents are reacted in DCM. The resultant resins 15 are washed with DMF and DCM.

Unique tagging of the supports in each reaction vessel is achieved with combinations of identifiers encoded in a binary scheme, e.g., as depicted in Table 5 for 15 choices of $R^4$. The identifiers are attached by adding a solution of up to two identifiers in DCM (in a 7.5–15% wt./wt. identifier: solid support ratio, depending on the signal strength of the identifier) to a batch of supports suspended in ethyl acetate or DCM and shaking the mixture for 0.5–1 hr. A dilute solution of rhodium trifluoroacetate dimer is added and the mixture is immediately shaken overnight. The resin is then washed in DCM, methanol, and DCM. The procedure is repeated as necessary to add additional identifiers.

The tagged resins 15 are then pooled and mixed. This mixed resin 15 is divided into two portions. One portion is taken through the chemistry described in Scheme 6 producing a library as given in Example 1. Another portion is taken through the chemistry described in Schemes 7, 8, and 9 producing a library as given in Example 2. Thus two libraries are produced which share synthons $R^1$, $R^4$, and the amino acid residue in common with one another.

Scheme 6

The mixed resin-bound aryliodides 15 are split into a predetermined number of reaction vessels. In this instance, since twenty-five aryl coupling reagents are used in the fourth combinatorial step, in twenty-five reaction vessels are placed equal portions of resin. Each resin is reacted with an aryl boronic acid, borane, or aryl zinc bromide (e.g. Tables 6 and 7). The arylboronic acids and boranes are coupled with resin 15 by treatment with tetrakistriphenylphosphine palladium and potassium carbonate in DMF. The aryl zinc bromine is reacted with 15 and tetrakis(triphenylphosphine) palladium in DMF. The resultant product resins 16 are washed with DMF/water, DMF, a solution of diethyldithiocarbamic acid and DIEA in DMF, DMF, DCM and methanol.

Any acid-labile protecting groups may be removed at this stage by treating the resin 16 with dilute sulfuric acid in acetonitrile.

The resultant resin batches 16 may be then tagged as described above or retained separately as sub-libraries (as in example 1). Amides of Formula III may be cleaved from resin compounds 16 by exposing them to UV light (ca. 360 nm) for 15–180 minutes at 25–50° C. in a suitable solvent such as methanol.

Scheme 7

The mixed resin-bound aryliodides 15 are split into a predetermined number of reaction vessels. In this instance, since three formyl boronic acid coupling reagents are used in the fourth combinatorial step, in three reaction vessels are placed equal portions of resin. Each resin is reacted with a formyl aryl boronic acid, (e.g. Table 7) by treatment with tetrakis(triphenylphosphine)-palladium and potassium carbonate in DMF. The resultant product resins 17 are washed with DMF/water, DMF, a solution of diethyldithiocarbamic acid and DIEA in DMF, DMF, DCM and methanol.

Unique tagging of the supports in each reaction vessel is achieved with combinations of identifiers encoded in a binary scheme, e.g., as depicted in Table 7 for 3 choices of $R^9$. The identifiers are attached by adding a solution of up to two identifiers in DCM (in a 7.5–15% wt./wt. identifier: solid support ratio, depending on the signal strength of the identifier) to a batch of supports suspended in ethyl acetate or DCM and shaking the mixture for 0.5–1 hr. A dilute solution of rhodium trifluoroacetate dimer is added and the mixture is immediately shaken overnight. The resin is then washed in DCM, methanol, and DCM. The procedure is repeated as necessary to add additional identifiers.

Scheme 8

The mixed resin-bound aldehydes 17 are split into a predetermined number of reaction vessels. In this instance, since twenty individual reactions are used in the fifth combinatorial step, in twenty reaction vessels are placed equal portions of resin. Some of these portions can be reacted with amines (via reductive amination) to generate resin-bound secondary amines 18. In this instance, the mixture of resin-bound aldehydes 17 is treated with an unique amine (e.g. see Table 8) in TMOF to generate the imine which is reduced by a subsequent treatment of the resin with sodium cyanoborohydride in methanol/HOAc in the presence of the same amine. Washing with methanol, water, a solution of potassium carbonate in water, water, and methanol yields the resins 18. These batches 18 may be then tagged as described above, retained separately as sub-libraries, or reacted further as below.

The resin-bound secondary amine in some of the batches 18 may be acetylated with acetic anhydride and DIEA in DCM and then washed with DCM and methanol (as in some batches from example 2) generating resins 19. These batches 19 may be then tagged as described above or retained separately as sub-libraries (as in example 2).

Scheme 9

(a) The resin-bound aldehydes 17 may be reduced to resin-bound alcohols 20 by treatment with sodium cyanoborohydride in methanol/HOAc. After washing with methanol, water, a solution of potassium carbonate in water, water, and methanol, this batch 20 may be tagged as described above or retained separately as sub-library (as in example 2).

(b and c) The resin-bound aldehydes 17 may undergo aldol reactions either prior or subsequent to their conversion into an imine. Conversion to the imine is completed as describe above via resin treatment with an amine (e.g. benzylamine in example 2) in TMOF. The aldol reaction is completed on the resin-bound aldehyde 17 or its imine by treatment with a silyl enol ether (e.g. methyl trimethylsilyl dimethylketene acetal in example 2) in the presence of scandium triflate in DCM. The resultant resin is washed with DCM, methanol, water, and methanol. The generated resins 21 and 22 can then be tagged as described above or retained separately as sub-libraries (as in example 2).

(d) The resin-bound aldehydes 17 may be converted to their homoallylic alcohols by treatment with allyl bromide and indium metal in THF/water. The resin is then washed with THF/water, methanol, DCM, and methanol. The resultant resin 23 may be tagged as described above or retained separately as sub-library (as in example 2).

(e) The resin-bound aldehydes 17 may be reacted under Wittig conditions to generate resin-bound olefins. In an example of such a reaction, a t-butyl ester is prepared by treatment with (t-butoxycarbonylmethylene)-triphenylphosphorane in THF. After washing with THF, DCM, and methanol, the t-butyl ester may be cleaved with TFA/DCM. After washing with DCM and methanol, the resultant resin-bound carboxylic acid 24 may be tagged as described above or retained separately as sub-library (as in example 2).

Preferred amines for inclusion in the libraries to provide the residue $R^1$ are the amines shown in table 2.

Preferred aminoacid amides $R^2$ for inclusion in the libraries are:

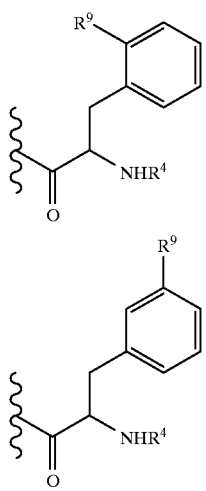

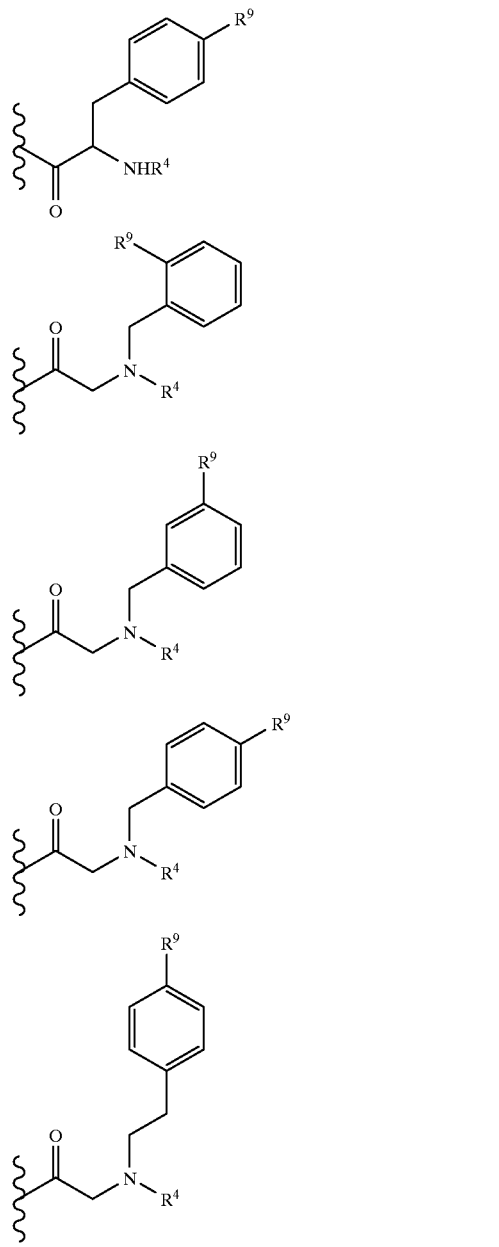

Preferred $R^4$ residues are as noted above in the summary. In these libraries, $R^9$ may be

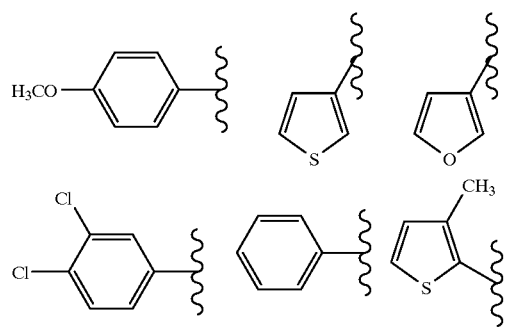

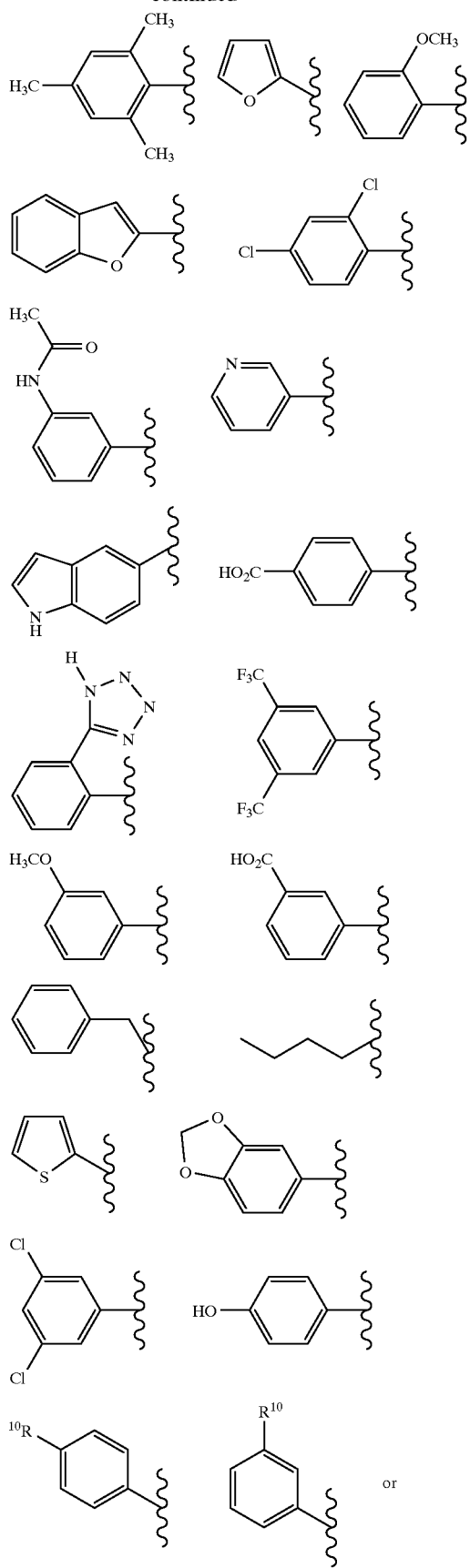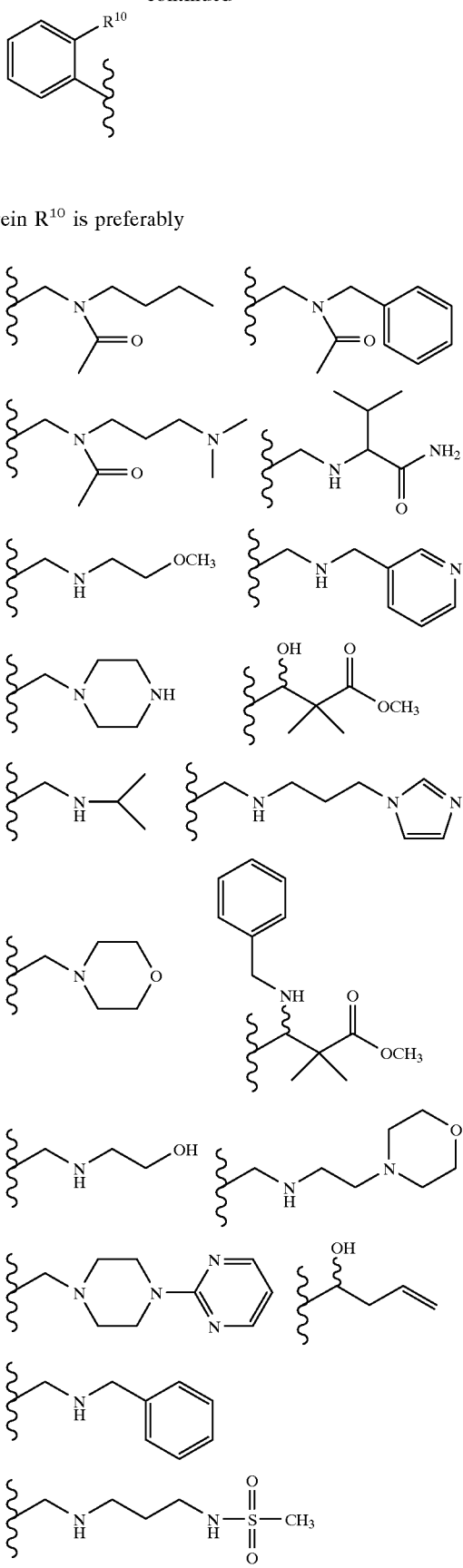
wherein R[10] is preferably
or

19

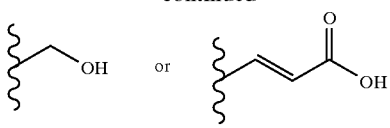

Preparation and Use of Identifiers
Identifiers are of the general formula X

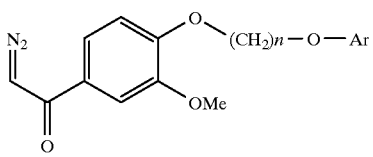

wherein:
n=4–12 and Ar is pentachlorophenyl or
n=3–6 and Ar is 2,4,6-trichlorophenyl. When the carbene, generated from diazoketone X, inserts into a C—H bond in the substrate, it produces an identifier residue T'-L of the formula II; when it adds across a double bond, it produces an identifier residue of formula IIa. Eleven compounds of the general formula X were prepared in accordance with the following illustrative example.

Step 1—1-hydroxy-9-(2,3,4,5,6-pentachlorophenoxy) nonane (1.634 g, 4.0 mmol), methyl vanillate (0.729 g, 4.0 mmol) and triphenylphosphine (1.258 g, 4.8 mmol) were dissolved in 20 mL dry toluene under argon. DEAD (0.76 mL, 0.836 g, 4.8 mmol) was added dropwise and the mixture was stirred at 25° C. for one hour. The solution was concentrated to half volume and purified by flash chromatography, eluting with DCM to yield 1.0 g (1.7 mmol, 43%) of the product as a white crystalline solid.

Step 2—The methyl ester product of step 1 (1.0 g, 1.7 mmol) was dissolved in 50 mL THF, 2 mL water was added, followed by LiOH (1.2 g, 50 mmol). The mixture was stirred at 25° C. for one hour then refluxed for 5 hours. After cooling to 25° C., the mixture was poured onto ethyl acetate (200 mL) and washed with 1 M HCl (3×50 mL), then saturated aqueous NaCl (1×50 mL) and then dried over sodium sulfate. The solvent was removed and the crude acid azeotroped once with toluene.

Step 3—The crude material from step 2 was dissolved in 100 mL toluene, and 10 mL (1.63 g, 14 mmol) thionyl chloride was added and the resulting mixture was refluxed for 90 minutes. The volume of the solution was reduced to approximately 30 mL by distillation, then the remaining toluene was removed by evaporation. The crude acid chloride was dissolved in 20 mL dry DCM and cooled to −70° C. under argon and a solution of approximately 10 mmol diazomethane in 50 mL anhydrous ether was added. The mixture was warmed to room temperature and stirred for 90 minutes. Argon was bubbled through the solution for 10 minutes, then the solvents were removed by evaporation and the crude material was purified by flash chromatography, eluting with 10–20% ethyl acetate in hexane. The diazoketone (0.85 g, 1.4 mmol, 82% yield over three steps) was obtained as a pale yellow solid.

An improvement was made to the final diazomethylation step, whereby the acid chloride was reacted with (trimethylsilyl)-diazomethane and triethylamine to give the identifier, which was then used without further purification.

20

This was a significant improvement over the original reaction with diazomethane, as the identifier was now obtained in high yield with no chloromethylketone by-product. Also, purification by flash chromatography was no longer necessary, which in some cases had resulted in significant acid-catalyzed decomposition of the identifier.

Alternate Step 3—5.7 mL (11.4 mmol, 3.00 eq.) of a 2.0 M solution of (trimethylsilyl)-diazomethane in hexanes was added to a solution of the acyl chloride (3.8 mmol, 1.00 eq.) and 1.85 mL (13.3 mmol, 3.5 eq.) of triethylamine in anhydrous THF/acetonitrile (1:1) at 0° C. under argon. The resulting orange solution was stirred at 0° C. for 2 hours, then at 25° C. for 17 hours. (If a precipitate immediately formed upon addition of the (trimethylsilyl)-dizomethane, DCM was added until the precipitate redissolved.) 250 mL of EtOAc was added and the organic layer was washed with 100 mL each of saturated aqueous $NaHCO_3$ and water, then dried with anhydrous $MgSO_4$. Removal of the volatiles in vacuo produced a yellow crystalline product at 60–100% yield.

In the synthesis of Example 1, 11 identifiers were used to encode the combinatorial library. In Step 1, pentachlorophenyl identifiers where n=9–12 (abbreviated $C_9Cl_5$, $C_{10}Cl_5$, $C_{11}Cl_5$, and $C_{12}Cl_5$) were used in the following binary encoding scheme: 0001=(n=12), 0010=(n=11), 0100=(n=10) and 1000=(n=9). In Step 2, pentachlorophenyl identifiers where n=6–8 (abbreviated $C_6Cl_5$, $C_7Cl_5$, and $C_8Cl_5$) were used and encoded as follows: 001=(n=8), 010=(n=7), 100=(n=6). In Step 3, trichlorophenyl identifiers where n=3–6 (abbreviated $C_3Cl_3$, $C_4Cl_3$, $C_5Cl_3$, and $C_6Cl_3$) were used in the following binary encoding scheme: 0001=(n=6), 0010=(n=5), 0100=(n=4) and 1000=(n=3).

Thus, in Step 1, reagent 3 (Table 3) is encoded "0011" which represents tagging this choice in the synthesis with two pentachlorophenyl identifiers where n=11 and 12. Likewise, in Step 2 reagent 4 (Table 4) is encoded "111" which designates tagging this choice in the synthesis with the pentachlorophenyl identifiers where n=6, 7 and 8. In a final example, in Step 3, reagent 5 (Table 5) is encoded "0101" which represents tagging this choice in the synthesis with two trichlorophenyl identifiers where n=4 and 6.

In the synthesis of Example 2, 13 identifiers were used to encode the combinatorial library. In Step 1, pentachlorophenyl identifiers where n=9–12 (abbreviated $C_9Cl_5$, $C_{10}C_{15}$, $C_{11}Cl_5$, and $C_{12}Cl_5$) were used in the following binary encoding scheme: 0001=(n=12), 0010=(n=11), 0100=(n=10) and 1000=(n=9). In Step 2, pentachlorophenyl identifiers where n=6–8 (abbreviated $C_6Cl_5$, $C_7Cl_5$, and $C_8Cl_5$) were used and encoded as follows: 001=(n=8), 010=(n=7), 100=(n=6). In Step 3, trichlorophenyl identifiers where n=3–6 (abbreviated $C_3Cl_3$, $C_4Cl_3$, $C_5Cl_3$, and $C_6Cl_3$) were used in the following binary encoding scheme: 0001=(n=6), 0010=(n=5), 0100=(n=4) and 1000=(n=3). Finally, in Step 4', pentachlorophenyl identifiers where n=4 and 5 (abbreviated $C_4Cl_5$ and $C_5Cl_5$) were used and encoded as follows: 01=(n=5) and 10=(n=4).

For instance, in example 2, Step 4', reagent 3 (Table 7) is encoded "11" which represents tagging this choice in the synthesis with two pentachlorophenyl identifiers where n=4 and 5.

EXAMPLE 1

39375 Compound Library

Step (1). Sequential attachment of Bis-Fmoc lysine, photolabile linker, $R^1$ amines, and encoding.

(a). Attachment of Bis-Fmoc lysine to TentaGel (Scheme 1). TentaGel resin 1 (S—$NH_2$, 90 g, 0.28 mmol/g, 25.2 mmol, 180–220 μm) was apportioned into fifteen reaction vessels. To each vessel containing TentaGel resin (6.0 g) was added a preformed DMF solution of bis-Fmoc lysine 2 (5.0 mmol, 3.0 g), HOBt (5.0 mmol, 0.69 g), and DIC (10.0 mmol, 1.58 mL). The suspension was shaken overnight, then drained and washed with DMF (3×80 mL), DCM (3×80 mL), and DMF (3×80 mL). The resultant ninhydrin-negative resin 3 was then encoded as below.

(b). Encoding of resin 3. Each of the fifteen batches in Step 1a were encoded prior to the addition of the photolabile linker and the first combinatorial step, with one or more of the $C_{12}Cl_5$-, $C_{11}Cl_5$-, $C_{10}Cl_5$- and $C_9Cl_5$-linker-diazoketones to produce the appropriate binary code. Resin was first washed with DCM (2×5 mL) and ethyl acetate (1×50 mL). Identifiers were then incorporated one or two at a time until the required binary code was completed. For example, resin batch 7 (6.0 g) was suspended in 100 mL of ethyl acetate, a solution of $C_{12}Cl_5$-linker-diazoketone (0.45 g; 7.5% of resin mass) dissolved in 5 mL DCM was added followed by a solution of $C_{11}Cl_5$-linker-diazoketone (0.45 g; 7.5% of resin mass) dissolved in 5 mL DCM. After agitation for 1 hr, rhodium trifluoroacetate dimer (10 mL of a 1.0 mg/mL solution in DCM) was added and the resin agitated 1 h. A second portion of each tag, $C_{12}Cl_5$-linker-diazoketone (0.45 g/5 mL DCM) and $C_{11}Cl_5$-linker-diazoketone (0.45 g/5 mL DCM), was added and the suspension was shaken at 25° C. overnight. The resin was then filtered and washed with 80 mL portions of DCM (3×), methanol (3×), DCM (3×) and ethyl acetate (1×). This resin batch was again suspended in 100 mL of ethyl acetate and a solution of $C_{10}Cl_5$-linker diazoketone (0.45 g) dissolved in 5 mL DCM was added. After agitation for 1 hr, rhodium trifluoroacetate dimer (10 mL of 1.0 mg/mL solution in DCM) was added. After 1 h agitation a second portion of $C_{10}Cl_5$-linker diazoketone (0.45 g/5 mL DCM) was added and the resin was agitated at rt overnight. The resin was then filtered and washed with 80 mL portions DCM (3×), methanol (3×), and DCM (3×).

(c). Removal of Fmoc and attachment of photolinker (Scheme 2a). Tagged resin 3 (6.0 g) was washed with DMF (2×80 mL), shaken in 20% piperidine/DMF for 1 h, drained, and washed with DMF (3×80 mL) and DCM (3×80 mL). The generated deprotected resin 4 was suspended in a preformed (30 min) solution of 4-bromomethyl-3-nitro benzoic acid 5 (10.1 mmol, 2.6 g), HOBt (10.1 mmol, 1.4 g), DIC (20.3 mmol, 3.2 mL) in DMF (5 mL)/DCM (42 mL). The suspension was shaken overnight, drained and washed with DMF (3×80 mL) and DCM (3×80 mL). This was repeated in parallel for each of the fifteen reaction vessels containing the tagged resin 3 to generate ninhydrin-negative resin 6.

(d). Amine addition (Scheme 2b). Each of the fifteen batches of resin 6 was reacted with one amine listed in Table 2. For example, to a suspension of the resin (6 g) in THF (50 mL) was added butylamine (7.1 mL, 72 mmol), and shaken overnight. The resin was then drained and washed with DMF (1×80 mL), 5% DIEA/DMF (1×80 mL), DMF (2×80 mL), and DCM (3×80 mL).

(e). Resin mixing. The resin was combined as a suspension in methanol, mixed to homogeneity (30 min), filtered and dried overnight in vacuo. Due to the large amount of resin, the resin was divided into 14 identical batches, two batches for each of the seven pieces to be added in combinatorial step two.

Step (2). Attachment of $R^2$ iodophenylalanine or N-iodoarylglycine pieces and encoding.

(a). Addition of $R^2$ Boc-iodophenylalanines (Scheme 3). The three iodophenylalanine pieces from Table 3 were each coupled to two batches of resin 7. (Hence, a total of three pieces were added to two vessels each, making a total of six vessels used.) For example, in vessels 3 and 4, resin 7 (6.8 g) was suspended in a preformed solution (3 min) of Boc-m-iodophenylalanine (4.5 g; 11.6 mmol), PyBroP (5.4 g; 11.6 mmol), and DIEA (4 mL; 23.1 mmol) in 50 mL of 10% DCM/DMF and the suspension was shaken overnight. The resin was then drained and washed with DMF (3×80 mL) and DCM (3×80 mL) to generate resin 9.

(b). Coupling of Bromoacetic acid and Addition of Iodoarylamines (Scheme 4). Bromoacetic acid was coupled to the resin in remaining eight vessels as in the following example. Resin 7 (6.8 g) was suspended in a preformed (stirred 30 minutes and filtered) solution of bromoacetic acid (5.4 g; 38.6 mmol) and DIC (6.1 mL; 38.6 mmol) in 50 mL DCM. After shaking overnight, the resin was drained and washed with DMF (3×80 mL), DCM (3×80 mL), DMF (1×80 mL), and DMSO (1×80 mL) to provide resin 11.

The four iodoarylamine pieces from Table 4 were each added to two batches of resin 11. (Hence, a total of four pieces were added to two vessels each, making a total of eight vessels used.) For example, resin 11 in vessels 7 and 8 was suspended in a DMSO solution of p-iodobenzylamine (4.5 g; 19.3 mmol) and DIEA (6.7 mL; 38.5 mmol) and shaken overnight. The resin was then drained and washed with DMSO (1×80 mL), DMF (3×80 mL), and DCM (3×80 mL) to yield resin 13.

(c). Encoding of resins 9 and 13. Each of the fifteen batches in Step 2 were at this stage encoded with one or more of the $C_8Cl_5$-, $C_7Cl_5$-, and $C_6Cl_5$-linker-diazoketones to produce the appropriate binary code. Resin 13 harboring secondary amines (vessels 7–14) was first protonated by shaking in 25%TFA/DCM (80 mL) for 15 min. The resin was then washed with DCM (3×80 mL). Identifiers were then incorporated one or two at a time until the required binary code was completed. For example, resin batch 7 (6.8 g) was suspended in 100 mL of ethyl acetate, a solution of $C_8Cl_5$-linker-diazoketone (0.45 g; 6.6% of resin mass) dissolved in 5 mL DCM was added followed by a solution of $C_7Cl_5$-linker-diazoketone (0.45 g; 6.6% of resin mass) dissolved in 5 mL DCM was added. After agitation for 1 hr, rhodium trifluoroacetate dimer (10 mL of a 1.0 mg/mL solution in DCM) was added and the resin agitated 1 h. A second portion of each tag, $C_8Cl_5$-linker-diazoketone (0.45 g/5 mL DCM) and $C_7Cl_5$-linker-diazoketone (0.45 g/5 mL DCM), was added and the suspension was shaken at rt overnight. The resin was then filtered and washed with 80 mL portions of DCM (3×), methanol (3×), and DCM (3×).

(d) Boc removal from resin 9. Each vessel containing resin 9 was treated with 25%TFA/DCM as in the following example. Vessel 1 was shaken with 25%TFA/DCM (80 mL) for 30 min, drained, and washed with DCM (3×80 mL), methanol (3×80 mL), and DCM (3×80 mL) yielding deprotected resin 10.

(e) Mixing and deprotonation of amines. All 14 vessels containing resins 10 and 13 were combined into one vessel and shaken with 5%DIEA/DCM (3×2 min) and then washed with DCM (2×80 mL) and methanol (3×80 mL). The resin was resuspended in methanol agitated for 30 min, drained, and dried overnight in vacuo to yield mixed resin 14. This resin was divided equally among 15 reaction vessels.

Step (3). Attachment of Amine capping reagents $R^3$ and encoding (Scheme 5).

The free amines of resin 14 were reacted with the reagents listed in Table 5 by one of the methods described below.

(a). HATU or PyBroP coupling. Reagents 5, 7, 8, 9, and 14 (Table 5) were reacted as in the following example.

Phenylacetic acid (2.5 g; 18.4 mmol), HATU (6.9 g; 18.4 mmol), and DIEA (6.3 mL; 36.4 mmol) were premixed in 50 mL DMF (3 min) and then this solution added to resin 14 (6.8 g) and shaken overnight. The resin was then drained and washed with DMF (3×80 mL) and DCM (3×80 mL). Reagent 6 was added in a similar fashion with the exception of substituting PyBroP for HATU.

(b) DIC coupling. Reagents 3 and 4 (Table 5) were reacted as in the following example. Resin 14 (6.8 g) was suspended in a preformed (stirred 20 minutes and filtered) solution of methoxyacetic acid (2.8 mL; 36 mmol) and DIC (5.7 mL; 36 mmol) in 50 mL DCM and shaken overnight. The vessel was subsequently drained and washed with DMF (3×80 mL) and DCM (3×80 mL).

(c) Acid chloride coupling. Reagents 2 and 13 were coupled as in the following example. Resin 14 (6.8 g) was suspended in DCM (50 mL), methanesulfonyl chloride (0.84 mL; 10.8 mmol) and DIEA (3.8 mL; 20.8 mmol) were added, and the resin was shaken overnight. The vessel was then drained and washed with DMF (3×80 mL) and DCM (3×80 mL).

(d) Anhydride coupling. Reagents 10 and 11 were coupled as in the following example. Resin 14 was suspended in a solution of succinic anhydride (1.8 g; 18 mmol) in 50/50 DCM/DMF (80 mL) and shaken overnight. The vessel was then drained and washed with DMF (3×80 mL) and DCM (3×80 mL). Reagent 15 was coupled by adding acetic anhydride (3.7 mL; 39.2 mmol) and DIEA (6.3 mL; 36 mmol) to a suspension of resin 14 (6.8 g) in DCM (50 mL).

(e) Isocyanate coupling. Reagents 1 and 12 were coupled as in the following example. Ethyl isocyanate (2.9 mL; 36 mmol) was added to a suspension of Resin 14 (6.8 g) in DCM (50 mL) and the vessel was shaken overnight. The vessel was subsequently drained and washed with DMF (3×80 mL) and DCM (3×80 mL).

(f). Encoding of resin 15. Each of the fifteen batches in Step 3 were encoded prior to mixing, with one or more of the $C_6Cl_3$-, $C_5Cl_3$-, $C_4Cl_3$- and $C_3Cl_3$-linker-diazoketones to produce the appropriate binary code. Identifiers were incorporated one or two at a time until the required binary code was completed. For example, resin batch 15 (6.8 g) was suspended in 100 mL of ethyl acetate, a solution of $C_6Cl_3$-linker-diazoketone (1.0 g; 15% of resin mass) dissolved in 10 mL DCM was added followed by a solution of $C_5Cl_3$-linker-diazoketone (1.0 g; 15% of resin mass) dissolved in 10 mL DCM. After agitation for 1 hr, rhodium trifluoroacetate dimer (10 mL of a 1.0 mg/mL solution in DCM) was added and the resin agitated overnight. The resin was then filtered and washed with 80 mL portions of DCM (3×), methanol (3×), DCM (3×) and ethyl acetate (1×). This resin batch was again suspended in 100 mL of ethyl acetate and a solution of $C_4Cl_3$-linker diazoketone (1.0 g) dissolved in 10 mL DCM and a solution of $C_3Cl_3$-linker diazoketone (1.0 g) dissolved in 10 mL DCM was added. After agitation for 1 hr, rhodium trifluoroacetate dimer (10 mL of 1.0 mg/mL solution in DCM) was added and the resin was agitated overnight. The resin was then filtered and washed with 80 mL portions DCM (3×), methanol (3×), DCM (3×).

(g). Resin mixing. The resin from the 15 vessels was combined as a suspension in methanol, mixed to homogeneity (30 min), filtered and dried overnight in vacuo. The dried resin 15 was divided into two portions. One portion (72.9 g) was set aside for the section of the library prepared in Example 2. Another portion of resin (30.3 g) was taken to the next step in this Example 1.

Step (4). Attachment of Aryl Coupling Reagents $R^4$ (Scheme 6).

Each of 25 batches (1.2 g each) of resin 15 was reacted with one aryl coupling reagent listed in Table 6. For example, resin 15 was suspended in 25 mL DMF and degassed by bubbling argon for 20 min. $Pd(PPh_3)_4$ (42 mg; 0.036 mmol) was then added and argon bubbling continued for 5 min. 4-Methoxybenzene boronic acid (220 mg; 1.45 mmol) and potassium carbonate (250 mg; 1.82 mmol) were then added and the vessel was shaken at 45° C. for 17 hr. At this time, the vessel was drained and washed with 50/50 DMF/water (4×30 mL) and DMF (3×30 mL). The resin was resubjected to the conditions outlined above and then washed with 50/50 DMF/water (4×30 mL), DMF (2×30 mL), 5% diethyldithiocarbamic acid/5%DIEA/DMF (2×30 mL), DMF (3×30 mL), DCM (3×30 mL), and methanol (3×30 mL). The resultant resin 16 was dried overnight in vacuo.

In another example (piece 23 from Table 6), resin 15 was suspended in 25 mL anhydrous THF and degassed by bubbling argon for 20 min. $Pd(PPh_3)_4$ (42 mg; 0.036 mmol) was then added and argon bubbling continued for 5 min. 10.8 mL of a 0.2 M benzyl zincbromide THF stock (prepared from equally molar portions of a 1 M benzylmagnesium chloride solution and anhydrous zinc bromide in THF) were added and the reaction was shaken at 45° C. overnight. The resin was then washed with DMF (3×30 mL), 5% diethyldithiocarbamic acid/5%DIEA/DMF (2×30 mL), DMF (3×30 mL), DCM (3×30 mL). and methanol (3×30 mL). The resultant resin 16 was dried overnight in vacuo.

Each of these final resin batches was individually stored as a separate sub-library obviating any encoding for Step 4.
Verification of Synthesis Several members from the library in Example 1 were synthesized on the solid phase to confirm the validity of the synthetic route and the identity of the final products. The compounds were cleaved from the resin via photoelution at 50° C. for 3–4 hr at 353 nm and the structures were confirmed by $^1$H NMR and mass spectroscopy.

EXAMPLE 2

94500 Member Library

Step (4'). Coupling of Formylbenzene Boronic Acids.

(a) Coupling of Formylbenzene Boronic Acids. 72.9 g of resin from step 3(g) above was divided into three equal portions (24.3 g) for the reaction of the three formylbenzene boronic acid pieces listed in Table 7. Due to the large amount of resin, coupling reactions were carried out in 3 shaker vessels (containing 8.1 g) for each piece. For example, resin 15 (8.1 g) was suspended in 125 mL DMF and degassed by bubbling argon for 20 min. $Pd(PPh_3)_4$ (281 mg; 0.24 mmol) was then added and argon bubbling continued for 5 min. 4-Formylbenzene boronic acid (1.46 g; 9.72 mmol) and potassium carbonate (1.68 g; 12.15 mmol) were then added and the vessel was shaken at 45° C. for 17 hr. At this time, the vessel was drained and washed with 50/50 DMF/water (4×30 mL) and DMF (3×30 mL). The resin was then resubjected to the conditions outlined above and finally washed with 50/50 DMF/water (4×30 mL), DMF (2×30 mL), 5% diethyldithiocarbamic acid/5%DIEA/DMF (2×30 mL), DMF (3×30 mL), DCM (3×30 mL), and methanol (3×30 mL).

(b). Encoding of resin 17. Each of the fifteen batches in Step 4' were at this stage encoded with one or more of the $C_5Cl_5$- and $C_4Cl_5$-linker-diazoketones to produce the appropriate binary code. Identifiers were then incorporated one or two at a time to complete the required binary code. For example, resin batch 9 (8.1 g) was suspended in 100 mL of DCM, a solution of $C_5Cl_5$-linker-diazoketone (0.61 g; 7.5% of resin mass) dissolved in 5 mL DCM was added followed by a solution of $C_4Cl_5$-linker-diazoketone (0.61 g; 7.5% of resin mass) dissolved in 5 mL DCM. After agitation for 1 hr, rhodium trifluoroacetate dimer (10 mL of a 1.0 mg/mL solution in DCM) was added and the resin agitated at rt overnight. The resin was then filtered and washed with 80 mL portions of DCM (3×), methanol (3×), DCM (3×).

(c). Resin mixing. The resin from the 9 vessels was combined as a suspension in methanol, mixed to homogeneity (30 min), filtered and dried overnight in vacuo. The dried resin 17 was divided into twenty equal portions.

Step (5) Reductive Amination, Acetylations, and Other Reactions (Schemes 8 and 9)

(a) Reductive Amination. 15 batches (3.55 g each) of resin 17 were reacted with one amine listed in Table 8. Reagent 5, benzylamine, was reacted with two resin batches, one of which was further acetylated as described below. For example, the resin (3.55 g) was shaken for 1 h in 25 mL TMOF containing methoxyethylamine (3.6 mL; 42 mmol). The vessel was drained and washed with 5% HOAc/methanol (1×25 mL). The resin was resuspended in 5%HOAc/methanol, methoxyethylamine (3.6 mL; 42 mmol) was re-added, and the vessel was shaken for 30 min. Sodium cyanoborohydride (2.64 g; 42 mmol) was then added and the reaction was shaken overnight. Subsequently, the resin was drained and washed with methanol (2×30 mL), water (2×30 mL), 15% potassium carbonate solution (1×30 mL), water (2×30 mL), methanol (4×30 mL).

(b) Vessels containing secondary amines arising from the reaction of butylamine, benzylamine, and 3-(dimethylamino)propylamine were acetylated as in the following example. Resin from step 5a (3.55 g) was shaken in DCM (30 mL), acetic anhydride (2 mL; 21.3 mmol) and DIEA (5.5 mL; 32 mmol) overnight. The vessel was then drained and washed with DCM (3×80 mL) and methanol (3×80 mL).

(c) Reduction ofthe resin-bound aldehyde. Resin 17 (3.55 g) was suspended in 25 mL 5% HOAc/methanol, sodium cyanoborohydride (2.64 g; 42 mmol) was added and the reaction was shaken overnight. Subsequently, the resin was drained and washed with methanol (2×30 mL), water (2×30 mL), 15%potassium carbonate (1×30 mL), water (2×30 mL), methanol (4×30 mL).

(d) Aldol reaction of resin-bound aldehyde. Resin 17 (3.55 g) was suspended in DCM (25 mL) and scandium triflate (1.05 g; 2.13 mmol) was added. After a 5 min shake, methyl trimethylsilyl dimethylketene acetal (4.3 mL; 21.3 mmol) was added and the suspension was shaken for 5 h. A second portion of trimethylsilyl dimethylketene acetal was added at this time and the reaction was shaken overnight. The vessel was then drained and washed with DCM (3×30 mL), methanol (3×30 mL), water (3×30 mL), and methanol (3×30 mL).

(e) Aldol reaction of resin-bound imine. Resin 17 (3.55 g) was suspended in TMOF and benzylamine (4.7 mL; 42.6 mmol), shaken for 2 h, drained and washed with DCM (3×30 mL). The resultant resin was suspended in DCM (25 mL) and scandium triflate (1.05 g; 2.13 mmol) was added. After a 5 min shake, methyl trimethylsilyl dimethylketene acetal (4.3 mL; 21.3 mmol) was added and the suspension was shaken for 5 h. A second portion of trimethylsilyl dimethylketene acetal was added at this time and the reaction was shaken overnight. The vessel was then drained and washed with DCM (3×30 mL), methanol (3×30 mL), water (3×30 mL), and methanol (3×30 mL).

(f) Allylation of resin-bound aldehyde. Resin 17 (3.55 g) was suspended in a mixture of THF (71 mL) and water (71 mL). Indium powder (1.8 g; 15.7 mmol) and allyl bromide (2.2 mL; 25.4 mmol) were added and the reaction was sonicated for 6 hr. The reaction was then filtered and washed with 50/50 THF/water (7×30 mL), water (3×30 mL), methanol (3×30 mL), DCM (3×30 mL), and methanol (4×30 mL).

(g) Wittig reaction of resin-bound aldehyde. Resin 17 (3.55 g) was suspended in THF (25 mL) and (t-butoxycarbonylmethylene)-triphenylphosphorane (3.2 g; 8.52 mmol) was added. The mixture was shaken overnight, drained, and the resin was washed with THF (3×50 mL), DCM (3×50 mL) and methanol (3×50 mL). The resin was then treated with 50 mL of 50/50 TFA/DCM for 3 hr, drained, and washed with DCM (3×50 mL) and methanol (3×50 mL).

Each of these 20 final resin batches was dried overnight in vacuo and individually stored as a separate sub-library obviating any encoding for Step 5.

Verification of Synthesis

Several members from this library were synthesized on the solid phase to confirm the validity of the synthetic route and the identity of the final products. The compounds were cleaved from the resin via photoelution at 50° C. for 3–4 hr at 353 nm and the structures were confirmed by $^1$H NMR and mass spectroscopy.

EXAMPLE 3

Decoding Procedure

A bead is placed in a 1.3 mm diameter pyrex capillary with 2 μL of acetonitrile. Ceric ammonium nitrate solution (2 μL of a 0.1 M aq. solution) and hexane (3 μL) are added and the two-phase mixture centrifuged briefly. The tube is sealed and left at 35° C. for 16 hr., then opened. The organic layer is removed by syringe and mixed with 1 μL of N,O-bis(trimethylsilyl)acetamide. The silated tag solution (1 μL) is analyzed by GC with electron capture (EC) detection.

The GC analysis is performed with a Hewlett Packard 5890 plus gas chromatograph. On column injection into a 5 m, 0.32 mm retention gap connected to a 25 m, 0.2 mm crosslinked 5% phenylmethyl silicone column is used. The temperature and pressure programs for the analysis are 200–320° C., 15° C./min., then 320° C. for 10 min. and 20–40 psi at 2 psi/min, then 40 psi for 10 min. The EC detector is maintained at 400° C. and the auxiliary gas is set at 35 psi.

The identity of the library compound attached to the bead is ascertained based on the reagents utilized in the synthesis of such compound, which are readily determined from the binary codes associated, respectively, with each of the identifiers for such reagents, as characterized through the above procedure. The binary codes for the identifiers assigned to the various reagents are represented in the following tables.

TABLE 1

Linker Groups

| Linker Group, —L'— | Cleavage reagent |
|---|---|
| 1. (nitrobenzyl structure with NO$_2$ and B) | light |

TABLE 1-continued

Linker Groups

| Linker Group, —L'— | Cleavage reagent |
|---|---|
| 2. (2-nitrobenzyl carbonate, -O-C(O)-B) | light |
| 3. (2-nitrobenzyl, -CH(B)-) | light |
| 4. (RO-substituted phenyl-B) | Ce(NH$_4$)$_2$(NO$_3$)$_6$ |
| 5. (bromo-phenyl-B) | Li, Mg, or BuLi |
| 6. (benzyl ether-CH$_2$-B) | H$_3$O$^+$ |
| 7. (methoxybenzyl ether-CH$_2$-B, OMe) | H$_3$O$^+$ |
| 8. (furan-B) | 1) O$_2$ or Br$_2$, MeOH  2) H$_3$O$^+$ |
| 9. —CH=CH(CH$_2$)$_2$— | O$_3$, OsO$_4$/IO$_4^-$, or KMnO$_4$ |
| 10. —CH=CHCH$_2$— | O$_3$, OsO$_4$/IO$_4^-$, or KMnO$_4$ |
| 11. —CH$_2$CH=CH— | O$_3$, OsO$_4$/IO$_4^-$, or KMnO$_4$ |
| 12. —CH=CHCH$_2$B— | (Ph$_3$)PRhCl(H) |
| 13. —S—CH$_2$—B— | Hg$^{+2}$ |
| 14. (X-CH(CH$_2$B)-) | Zn or Mg |

TABLE 1-continued

Linker Groups

| Linker Group, —L'— | Cleavage reagent |
|---|---|
| 15. (HO-CH(CH$_2$B)-) | Oxidation, e.g., Pb(OAc)$_4$ or H$_5$IO$_6$ |

R = H or lower alkyl; B = O or NH; and X = electron withdrawing such as Br, Cl, and I.

⌇ = point of attachment to C(O)

TABLE 2

Amine Reagents (R$^1$) and Encoding Scheme

| Amine Reagent | Binary Code |
|---|---|
| 1. CH$_3$NH$_2$ | 0001 |
| 2. (cyclopropylmethylamine) | 0010 |
| 3. (butylamine) | 0011 |
| 4. H$_3$CO-CH$_2$CH$_2$-NH$_2$ | 0100 |
| 5. (tetrahydrofurfurylamine) | 0101 |
| 6. (bicyclic amine) | 0110 |
| 7. (phenylbutylamine) | 0111 |
| 8. (2-chlorobenzylamine) | 1000 |
| 9. (3,4-dichlorobenzylamine) | 1001 |
| 10. (4-methoxybenzylamine) | 1010 |

TABLE 2-continued

Amine Reagents (R¹) and Encoding Scheme

| | Amine Reagent | Binary Code |
|---|---|---|
| 11. | 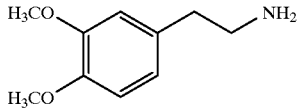 H₃CO, H₃CO — C₆H₃ — CH₂CH₂NH₂ | 1011 |
| 12. | 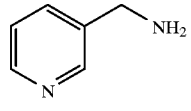 3-pyridyl-CH₂NH₂ | 1100 |
| 13. | 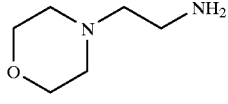 morpholino-CH₂CH₂NH₂ | 1101 |
| 14. | H₃CSO₂NH(CH₂)₃NH₂ | 1110 |
| 15. |  imidazolyl-(CH₂)₃NH₂ | 1111 |

TABLE 3

Boc-iodophenylalanine Reagents (R²) and Encoding Scheme

| | Iodophenylalanine Reagent | Binary Code |
|---|---|---|
| 1. | 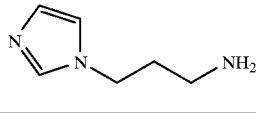 2-I-C₆H₄-CH₂-CH(NHBoc)-CO₂H | 001 |
| 2. | 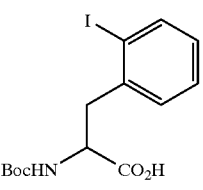 3-I-C₆H₄-CH₂-CH(NHBoc)-CO₂H | 010 |
| 3. | 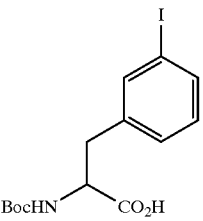 4-I-C₆H₄-CH₂-CH(NHBoc)-CO₂H | 100 |

TABLE 4

Iodoarylamine Reagents (R²) and Encoding Scheme

| | Iodophenylalanine Reagent | Binary Code |
|---|---|---|
| 1. | 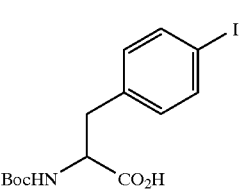 2-I-C₆H₄-CH₂NH₂ | 011 |
| 2. | 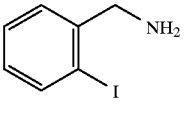 3-I-C₆H₄-CH₂NH₂ | 101 |
| 3. | 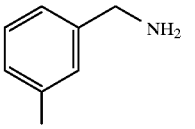 4-I-C₆H₄-CH₂NH₂ | 110 |
| 4. | 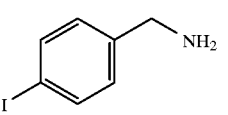 4-I-C₆H₄-CH₂CH₂NH₂ | 111 |

TABLE 5

Capping Reagents (R⁴) and Encoding Scheme

| | Capping Reagent | Binary Code |
|---|---|---|
| 1. | 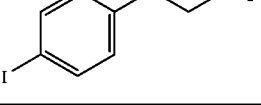 PhSO₂-N=C=O | 0001 |
| 2. | 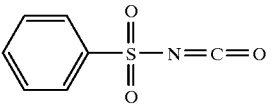 H₃C-SO₂-Cl | 0010 |
| 3. | 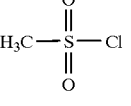 H₃CO-CH₂-CO-OH | 0011 |
| 4. | 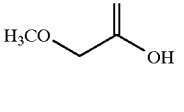 H₃CO-CH₂CH₂-O-CH₂-CO-OH | 0100 |
| 5. | 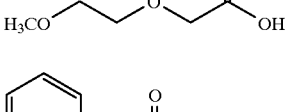 Ph-CH₂-CO-OH | 0101 |
| 6. | 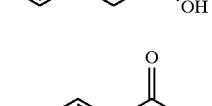 4-F-C₆H₄-CO-OH | 0110 |

TABLE 5-continued

Capping Reagents (R⁴) and Encoding Scheme

| | Capping Reagent | Binary Code |
|---|---|---|
| 7. | (CH₃)₂N-CH₂-C(=O)-OH | 0111 |
| 8. | imidazole-4-carboxylic acid | 1000 |
| 9. | nicotinic acid (pyridine-3-carboxylic acid) | 1001 |
| 10. | succinic anhydride | 1010 |
| 11. | diglycolic anhydride | 1011 |
| 12. | ethyl isocyanate (N=C=O) | 1100 |
| 13. | butyl chloroformate | 1101 |
| 14. | (CH₃)₂N-(CH₂)₃-C(=O)-OH | 1110 |
| 15. | acetic anhydride (H₃C-C(=O)-O-C(=O)-CH₃) | 1111 |

TABLE 6

Aryl Coupling Reagents (R⁹)
Aryl Coupling Reagents

| | | | | |
|---|---|---|---|---|
| 1. | H₃CO-C₆H₄-B(OH)₂ | | 8. | 3-methylthiophene-2-B(OH)₂ |
| 2. | C₆H₅-B(OH)₂ | | 9. | benzofuran-2-B(OH)₂ |
| 3. | 2-OCH₃-C₆H₄-B(OH)₂ | | 10. | indole-5-B(OH)₂ |
| 4. | pyridine-3-B(Et)₂ | | 11. | 3-H₃CO-C₆H₄-B(OH)₂ |
| 5. | 3,5-(F₃C)₂-C₆H₃-B(OH)₂ | | 12. | 1,3-benzodioxole-5-B(OH)₂ |

TABLE 6-continued
Aryl Coupling Reagents (R⁹)
Aryl Coupling Reagents
| 6. | 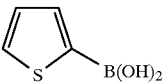 | 13. | 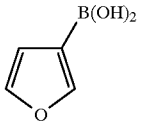 |
| 7. | 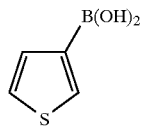 | 14. | 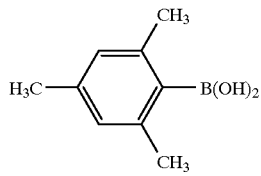 |
| 15. | 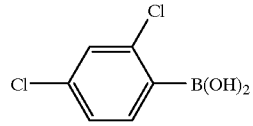 | 22. | 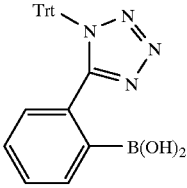 |
| 16. |  | 23. | 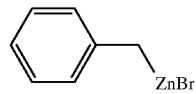 |
| 17. | 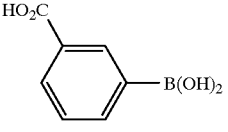 | 24. | 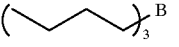 |
| 18. | 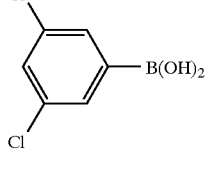 | 25. | 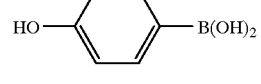 |
| 19. | 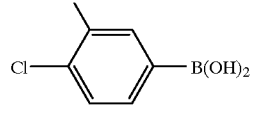 | | |
| 20. | 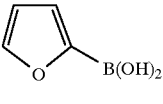 | | |
| 21. | 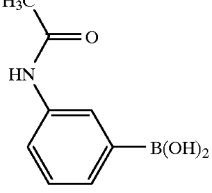 | | |

TABLE 7
Formyl Boronic acid Reagents (R⁹) and Encoding Scheme
| Formyl Boronic Acid Reagent | Binary Code |
|---|---|
| 1. 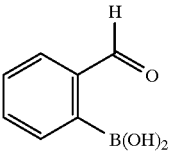 | 01 |
| 2. 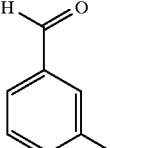 | 10 |
TABLE 7-continued
Formyl Boronic acid Reagents (R⁹) and Encoding Scheme
| Formyl Boronic Acid Reagent | Binary Code |
|---|---|
| 3. 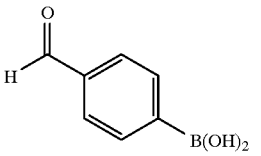 | 11 |
TABLE 8
Amine Reagents ($R^{11}$)
Amine Reagents
| | | | |
|---|---|---|---|
| 1. | 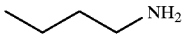 | 8. | 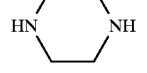 |
| 2. | 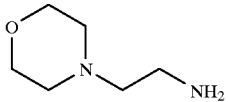 | 9. | 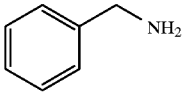 |
| 3. | 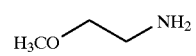 | 10. | 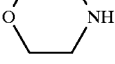 |
| 4. | 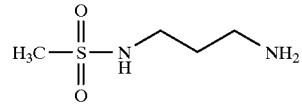 | 11. | 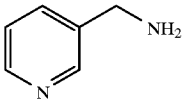 |
| 5. | 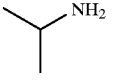 | 12. | 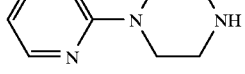 |
| 6. | 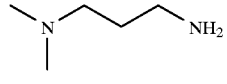 | 13. | 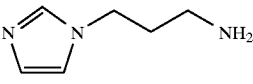 |
| 7. | 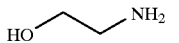 | 14. | 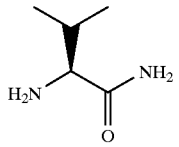 |

Scheme 1
Attachment of bis-Fmoc Lysine to Resin
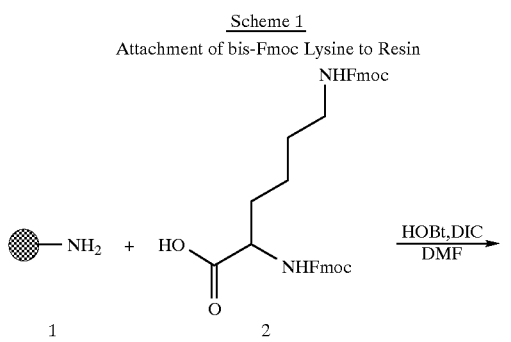
Scheme 2
Attachment of BNB Linker and Addition of Amines (R)
a. BNB attachment
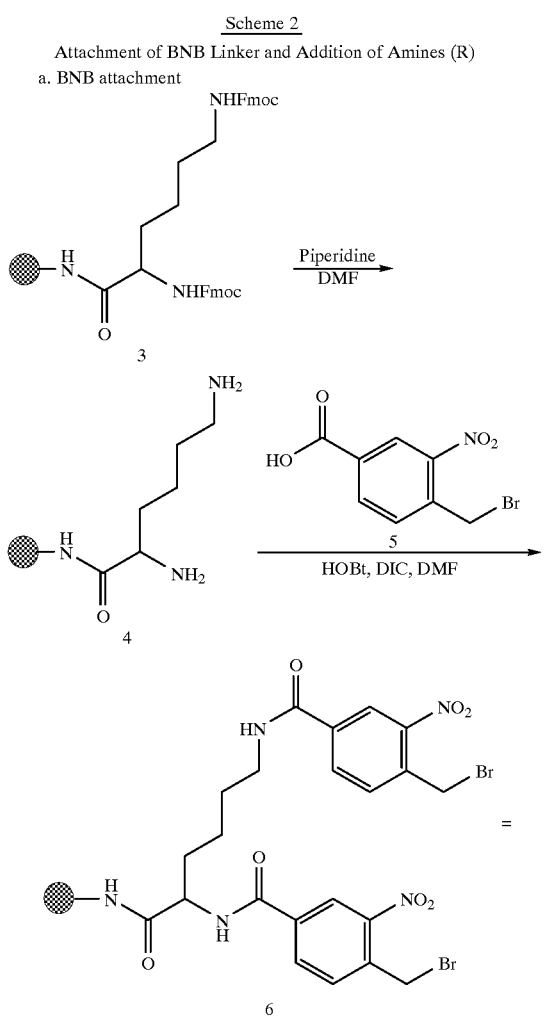
b. Amine (R¹) attachment
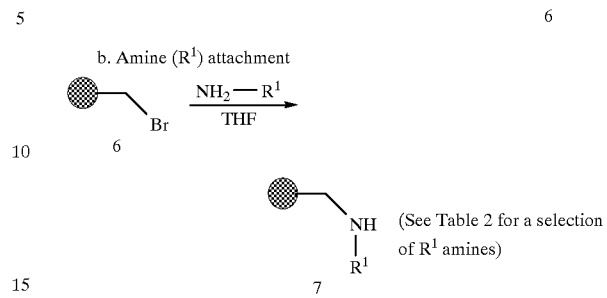
(See Table 2 for a selection of R¹ amines)
Scheme 3
Attachment of Boc-Iodophenylalanines and Boc Removal
a. Attachment of Boc-iodophenylalanines
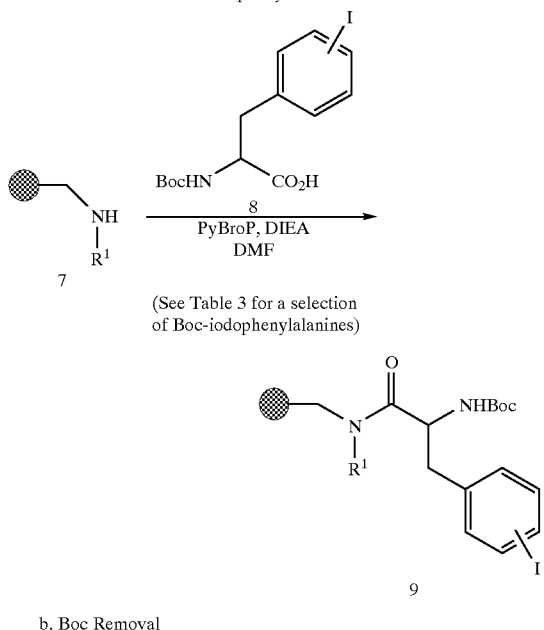
(See Table 3 for a selection of Boc-iodophenylalanines)
b. Boc Removal
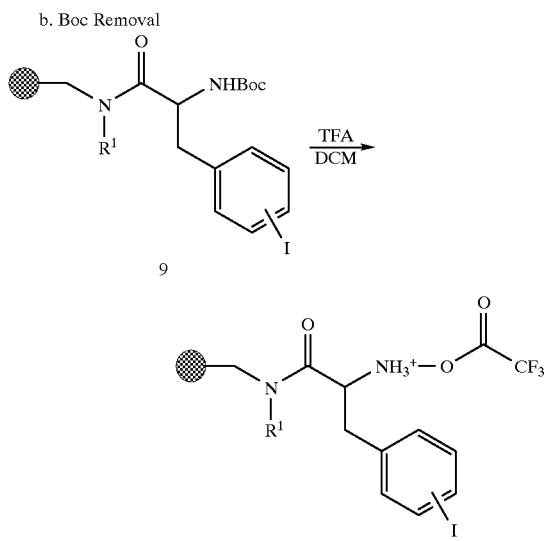

Scheme 4
Attachment of Bromoacetate and Addition of Iodoarylamine a. Attachment of Bromoacetate

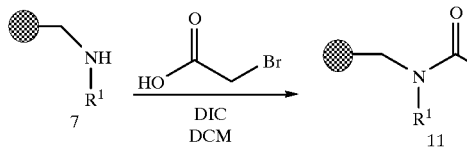

b. Iodoarylamine addition

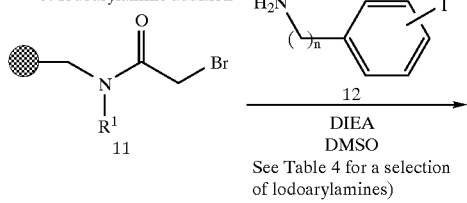

See Table 4 for a selection of Iodoarylamines)

Scheme 6
Attachment of Aryl Coupling Reagents ($R^9$)

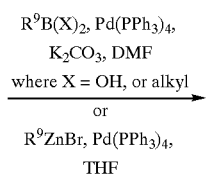

$R^9B(X)_2$, $Pd(PPh_3)_4$, $K_2CO_3$, DMF
where X = OH, or alkyl
or
$R^9ZnBr$, $Pd(PPh_3)_4$, THF (See Tables 6 and 7 for a selection of Aryl Coupling Reagents)

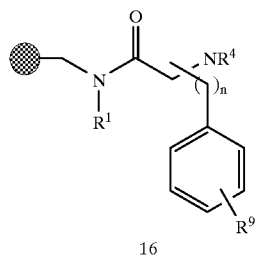

Scheme 5
Attachment of Capping Reagents ($R^4$)

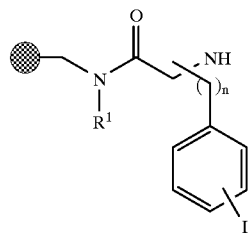

14
(10 and 13 combined)

$R^4CO_2H$, HATU (or PyBroP), DIEA, DMF
or
$R^4CO_2H$, DIC, DCM
or
$R^4NCO$, DCM
or
$R^4SO_2Cl$, DIEA; DCM
or
$R^4$-Anhydride, DCM

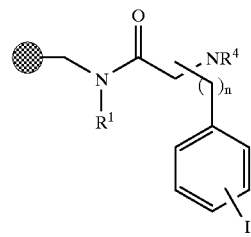

15

(See Table 5 for a selection of capping reagents)

Scheme 7
Coupling of Formyl Boronic Acids ($R^9$)
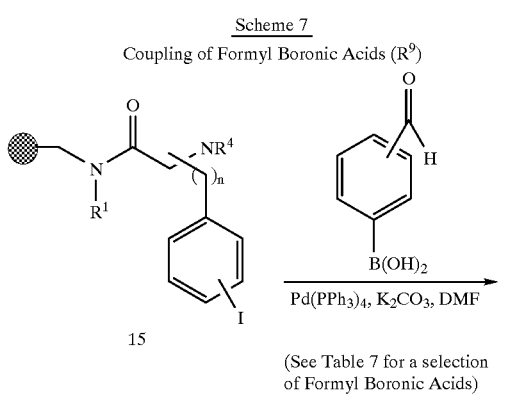
15
(See Table 7 for a selection of Formyl Boronic Acids)
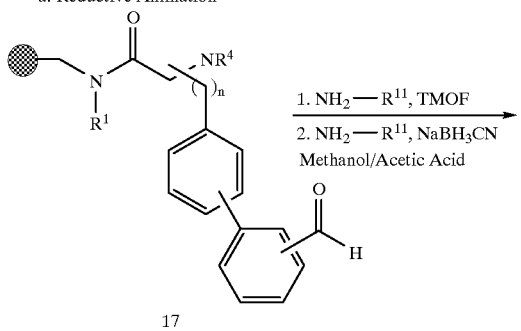
17
Scheme 8
Reductive amination of aldehyde ($R^{11}$)
a. Reductive Amination
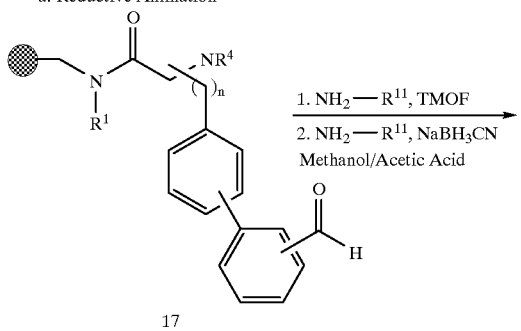
17
(See Table 8 for a selection of $R^{11}$ amines)
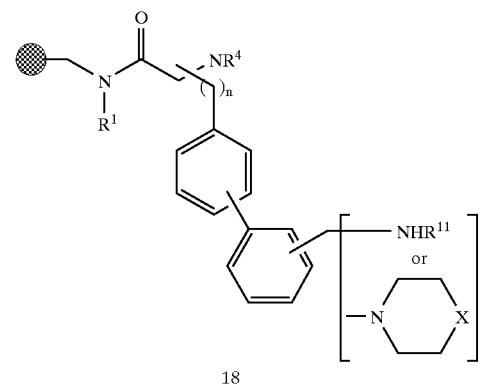
18
b. Acetylation of Selected Vessels
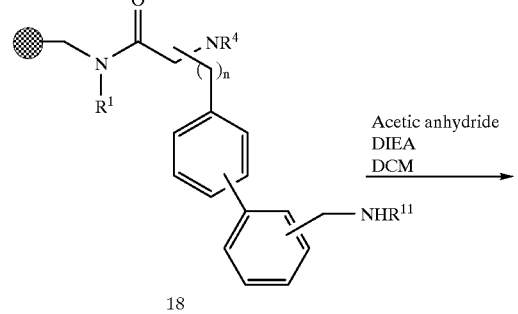
18
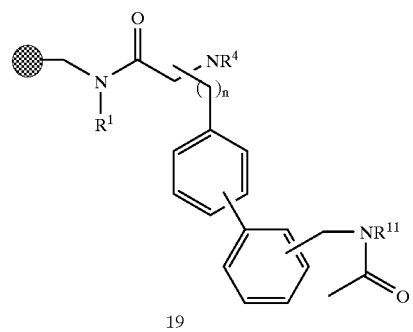
19

Scheme 9
Reactions of Resin Bound Aldehyde ($R^{10}$ = CHO)
(a) Reduction to Alcohol
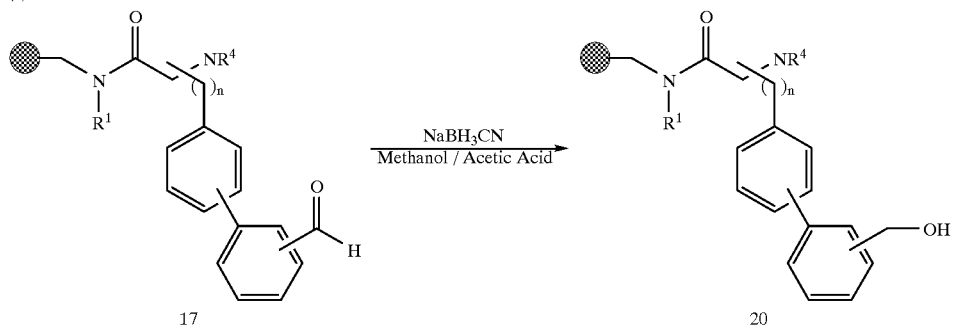
(b) Aldol Reaction
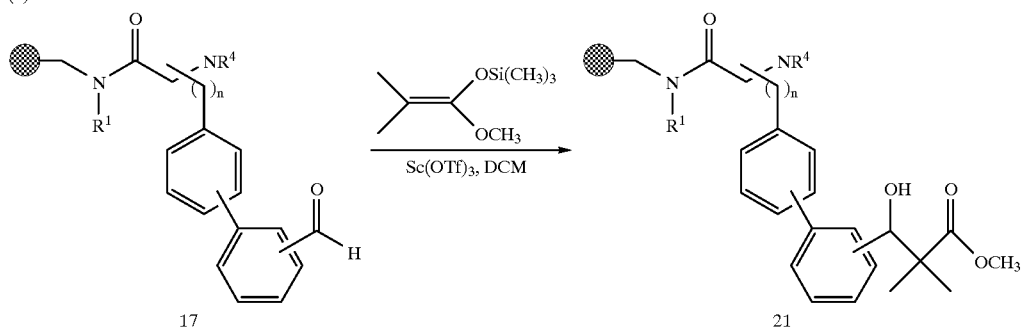
(c) Aldol Reaction on Imine
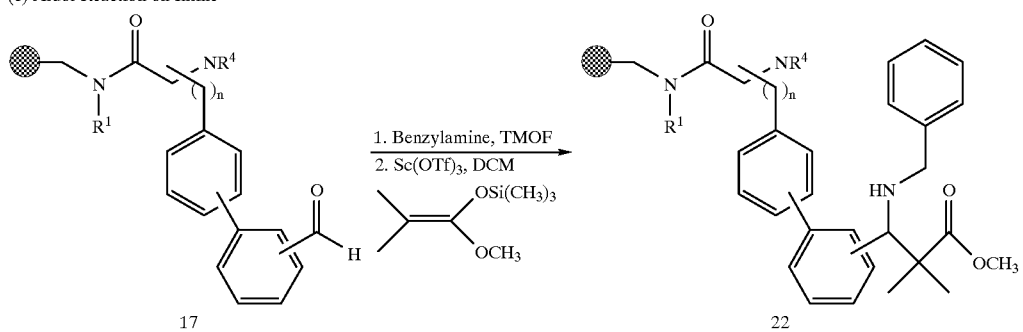
(d) Formation of Homoallylic Alcohol
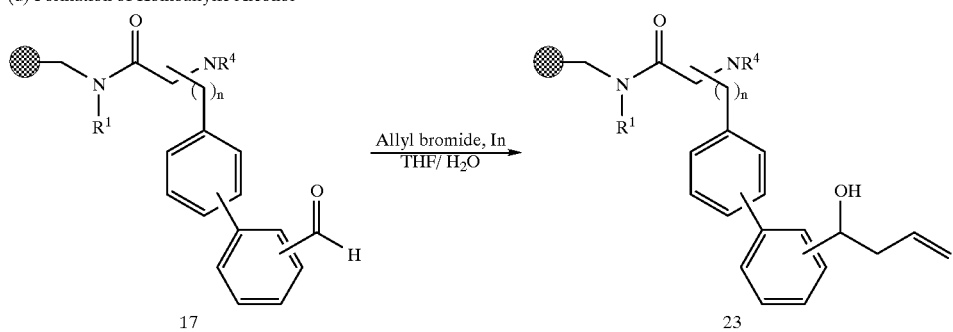

(e) Wittig Reaction

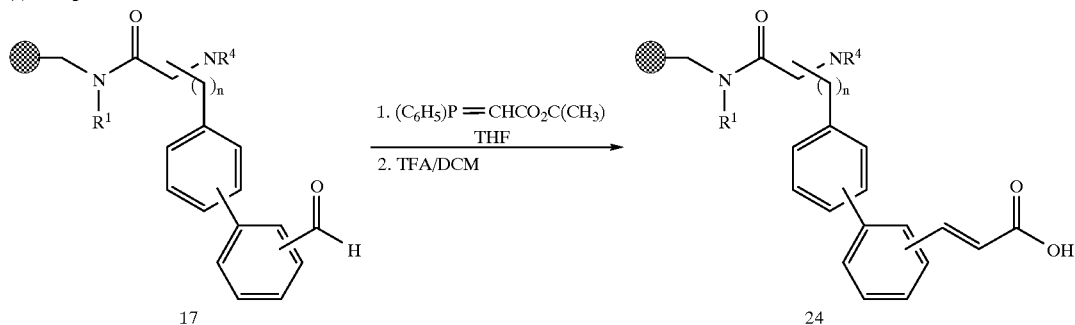

We claim:

1. A combinatorial chemical library comprising a plurality of members of the Formula I:

$$(T\text{-}L)_q\text{-}[S]\text{-}C(O)\text{-}L'\text{-}Z \qquad I$$

or I'

$$[S]\text{-}C(O)\text{-}L'\text{-}Z \qquad I'$$

wherein:

[S] is a solid support;

T' is an identifier residue;

L is a first linker;

L' is a second linker;

Z is $-NR^1R^2$;

q is 2–30;

$R^1$ is chosen from the group consisting of: H, $C_1$ to $C_{20}$ hydrocarbon, heteroaralkyl, heterocycloalkyl, substituted arylalkyl, alkoxyalkyl or alkyl-$SO_2NH$-alkyl;

$R^2$ is chosen from the group consisting of:

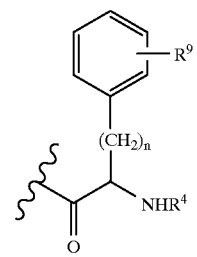

and

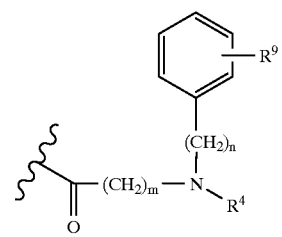

$R^4$ is chosen from the group consisting of: $-COR^5$, $-COOR^5-CO-(CH_2)_pR^6$, $-SO_2R^7$, $-CONHSO_2R^7$, and $-CONHR^7$;

$R^5$ is chosen from the group consisting of: alkyl, substituted alkyl, cycloalkyl, heterocycloalkyl, aryl, aralky, heteroaryl, and heteroaralkyl;

$R^6$ is chosen from the group consisting of: alkoxy, alkoxy-$CH_2(CH_2)_pO-$, aryl, heteroaryl, dialkylamino, $-CH_2CO_2R^8$, and $-OCH_2CO_2R^8$;

$R^7$ is chosen from the group consisting of: alkyl, aryl, and aralkyl;

$R^8$ is chosen from the group consisting of: H and alkyl;

$R^9$ is chosen from the group consisting of: alkyl, aralkyl, aryl, heteroaryl, and

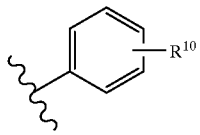

$R^{10}$ is chosen from the group consisting of $CH_2NHR^{11}$, $-NH$-acyl, $-CH_2OH$, aryl, cycloalkyl, hydroxyl, tetrazol-2-yl, aralkyl, carboxyl, 1-(trityl)tetrazol-2-yl, $-CH(OH)C(CH_3)_2CO_2R^8$, $-CHO$, $-CH(OH)CH_2CH=CH_2$, $-CH[NH(CH_2)_sR^{12}]C(CH_3)_2CO_2R^8$, $-CH=CHR^{16}$ and

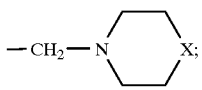

$R^{11}$ is chosen from the group consisting of: alkyl, $-CH_2(CH_2)_s$-alkoxy, $-(CH_2)_sCH_2OH$, aralkyl, -alkyl-$NHSO_2$-alkyl, heteroaralkyl, $-(CH_2)_sCH_2NR^{12}R^{12}$, $-CH(R^{15})CONR^{13}R^{14}$, and

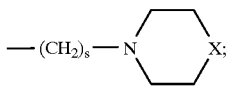

$R^{12}$ is independently chosen from the group consisting of alkyl, aryl and aralkyl;

$R^{13}$ and $R^{14}$ are independently chosen from the group consisting of H, alkyl, and aralkyl;

$R^{15}$ is chosen from the group consisting of: H, alkyl, cycloalkyl, aralkyl, aryl, and heteroaryl;

$R^{16}$ is chosen from the group consisting of: $C_1$ to $C_{20}$ hydrocarbon, heteroaryl and $COOR^8$;

X is chosen from the group consisting of: $CH_2$, O, S, and $NR^{15}$; and m, n, p and s are independently 1–4.

47

2. A library according to claim 1 comprising a plurality of members of formula I or I', wherein:

R⁵ is chosen from the group consisting of: lower alkyl and substituted alkyl;

R⁷ is chosen from the group consisting of: lower alkyl and aryl;

R⁸ is chosen from the group consisting of: H and lower alkyl;

R⁹ is chosen from the group consisting of: alkyl, aralkyl, aryl, heteroaryl, and

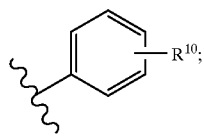

R¹⁰ is chosen from the group consisting of: CH₂NHR¹¹, —NH-acyl, —CH₂OH, carboxyl, —CH(OH)CH₂CH=CH₂, —CHO, hydroxyl, tetrazol-2-yl, 1-(trityl)tetrazol-2-yl, —CH=CHCOOR⁸, —CH(OH)C(CH₃)₂CO₂R⁸, —CH[NH(CH₂)ₛR¹²]C(CH₃)₂CO₂R⁸, and

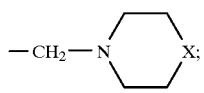

R¹² is chosen from the group consisting of: lower alkyl and aryl;

R¹³ and R¹⁴ are H;

R¹⁵ is chosen from the group consisting of: H and heteroaryl;

X is chosen from the group consisting of: O and NR¹⁵;

m and p are 1; and n and s 1 or 2.

3. A combinatorial library according to claim 1 comprising a plurality of members of formula I or I', wherein R¹ is chosen from the group consisting of: methyl; cyclopropylmethyl; butyl; methoxyethyl; tetrahydrofuran-2-ylmethyl; cis-myrtanyl, 4-phenylbutyl; 2-chlorobenzyl; 3,4-dichlorobenzyl; 4-methoxybenzyl; 3,4-dimethoxyphenethyl, 3-picolyl, N-morpholinylethyl; methylsulfonamidopropyl; and 1-imidazolylpropyl.

4. A combinatorial library according to claim 1 comprising a plurality of members of formula I or I', wherein R⁴ is chosen from the group consisting of:

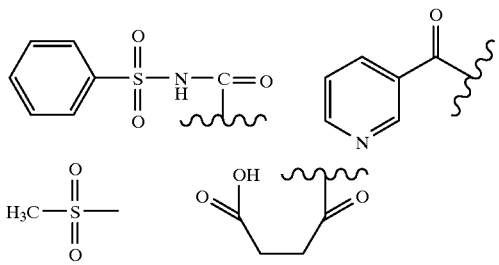

48

-continued

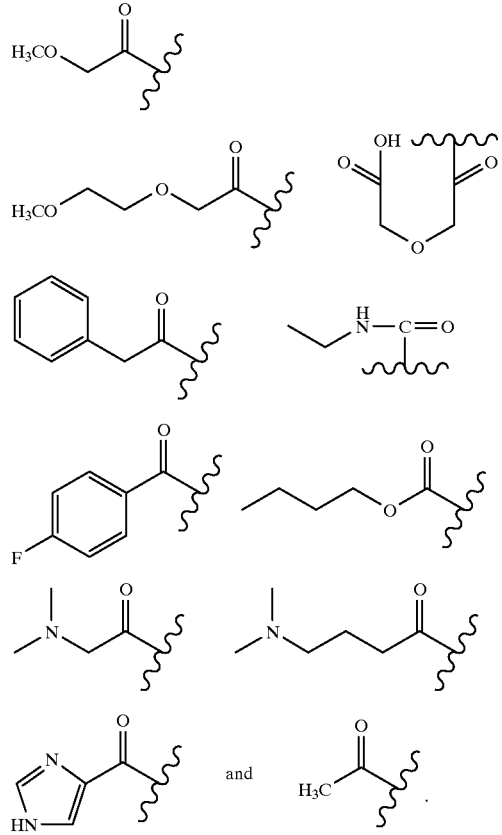

5. A combinatorial library according to claim 1 comprising a plurality of members of formula I or I', wherein R⁹ is chosen from the group consisting of: 4-methoxyphenyl; phenyl; 2-methoxyphenyl; pyridin-3-yl; 3,5-bis(trifluoromethyl)phenyl; thien-2-yl; thien-3-yl; 3-methylthien-2-yl; benzofuran-2-yl; indol-5-yl; 3-methoxyphenyl; 3,4-methylenedioxyphenyl; furan-3-yl; 2,4,6-trimethylphenyl; 2,4-dichlorophenyl; 4-carboxyphenyl; 3-carboxyphenyl; 3,5-dichlorophenyl; 3,4-dichlorophenyl; furan-2-yl; 3-acetamidophenyl; tetrazol-2-yl; 2-(tetrazol-2-yl)phenyl; benzyl; butyl; and 4-hydroxyphenyl.

6. A combinatorial library according to claim 1 comprising a plurality of members of formula I or I', wherein R⁹ is

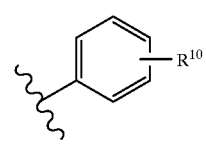

R¹⁰ is CH₂NHR¹¹ or —CH₂N(acetyl)R¹¹; and

R¹¹ is chosen from the group consisting of butyl, methoxyethyl, isopropyl, 2-hydroxyethyl, benzyl, 3-picolinyl, 3-(1-imidazolyl)propyl; N-morpholinylethyl; methylsulfonamidopropyl; 3-(dimethylamino)propyl; and

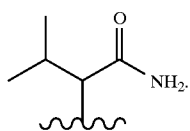

7. A combinatorial library according to claim 1 comprising a plurality of members of formula I or I', wherein $R^9$ is

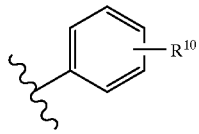

and $R^{10}$ is chosen from the group consisting of:

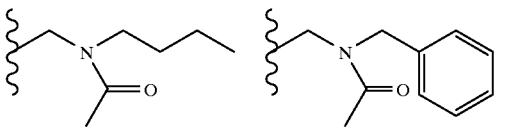

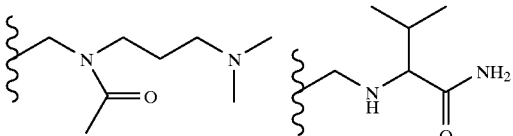

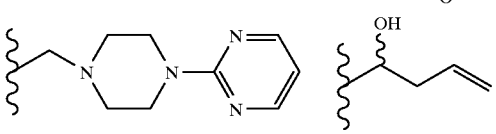

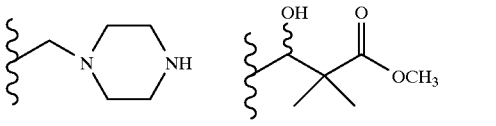

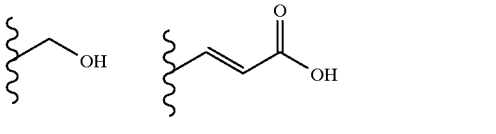

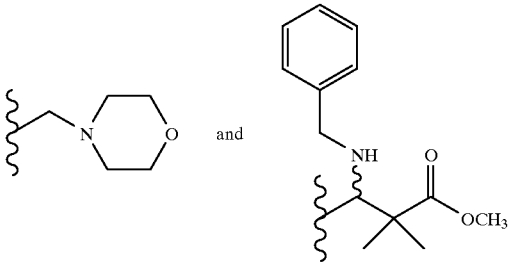

8. A combinatorial library according to claim 1 comprising a plurality of members of formula I or I' wherein:
$R^1$ is chosen from the group consisting of: methyl; cyclopropylmethyl; butyl; methoxyethyl; tetrahydrofuran-2-ylmethyl; cis-myrtanyl; 4-phenylbutyl; 2-chlorobenzyl; 3,4-dichlorobenzyl; 4-methoxybenzyl; 3,4-dimethoxyphenethyl, 3-picolyl, N-morpholinylethyl; methylsulfonamidopropyl; and 1-imidazolylpropyl;

$R^4$ is chosen from the group consisting of:

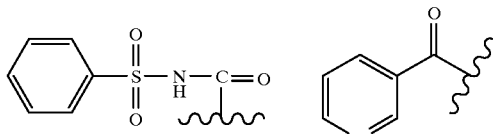

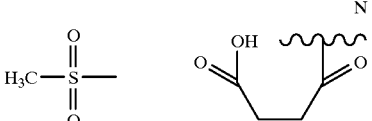

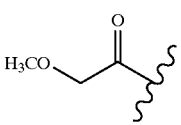

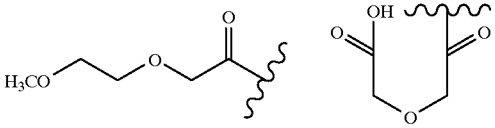

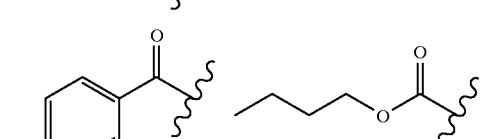

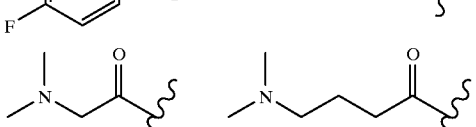

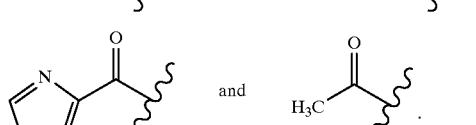

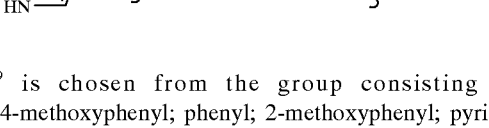

$R^9$ is chosen from the group consisting of: 4-methoxyphenyl; phenyl; 2-methoxyphenyl; pyridin-3-yl; 3,5-bis(trifluoromethyl)phenyl; thien-2-yl; thien-3-yl; 3-methylthien-2-yl; benzofuran-2-yl; indol-5-yl; 3-methoxyphenyl; 3,4-methylenedioxyphenyl; furan-3-yl; 2,4,6-trimethylphenyl; 2,4-dichlorophenyl; 4-carboxyphenyl; 3-carboxyphenyl; 3,5-dichlorophenyl; 3,4-dichlorophenyl; furan-2-yl; 3-acetamidophenyl; (tetrazol-2-yl)phenyl; benzyl; butyl; and 4-hydroxyphenyl; or $R^9$ is

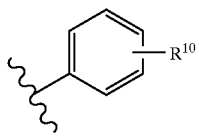

and $R^{10}$ is chosen from the group consisting of —$CH_2NHR^{11}$

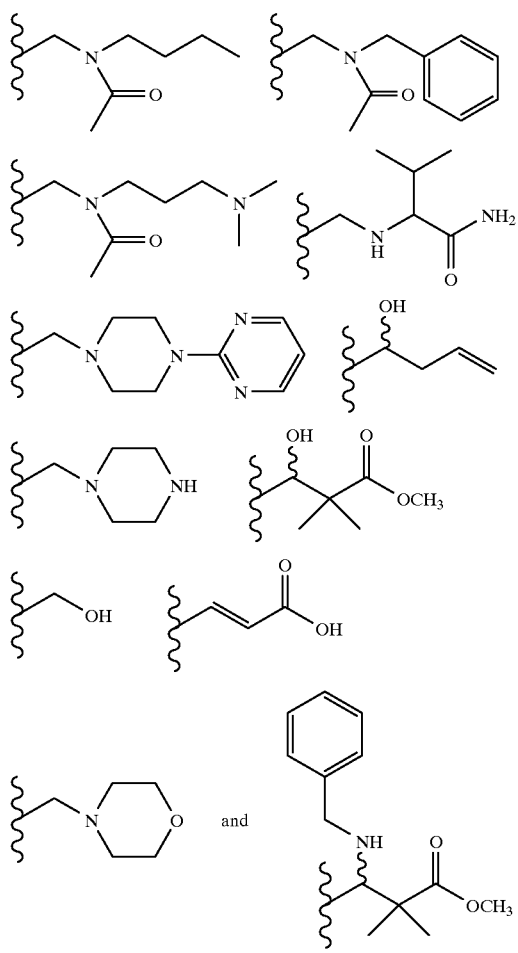

and $R^{11}$ is chosen from the group consisting of: methoxyethyl, isopropyl, 2-hydroxyethyl, benzyl, 3-picolinyl, 3-(1-imidazolyl)propyl; N-morpholinylethyl and methylsulfonamidopropyl.

9. A library according to claim 1 of Formula I comprising a plurality of members wherein the combination of T' and L is of the Formula

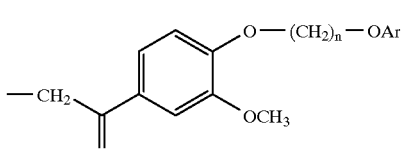

II or

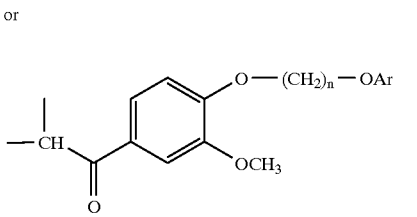

IIa n is 3–12;
Ar is halophenyl; and
q is 3–12.

10. A library according to claim 1 of Formula I or formula I' wherein -L'- is

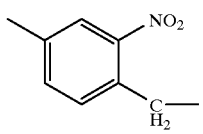

such that the left-hand bond as shown is the point of attachment to —C(O)— and the right hand bond is the point of attachment to -Z.

* * * * *

UNITED STATES PATENT AND TRADEMARK OFFICE
CERTIFICATE OF CORRECTION

PATENT NO. : 5,948,696
DATED : September 7, 1999
INVENTOR(S) : Dolle, III et al.

It is certified that error appears in the above-identified patent and that said Letters Patent is hereby corrected as shown below:

Col. 1, line 51, Formula I, delete "(T-L)" and replace with --(T'-L)--.

Col. 28, line 14, Table I, after "withdrawing", insert --group--.

Col. 37, line 30, Scheme 2, delete "(R)" and replace with --($R^1$)--.

IN THE CLAIMS:

Claim 1, Col. 45, line 21, delete "(T-L)" and replace with --(T'-L)--.

Signed and Sealed this

Twenty-first Day of March, 2000

Attest:

Attesting Officer

Q. TODD DICKINSON

Commissioner of Patents and Trademarks